US009176032B2

(12) United States Patent
Sood et al.

(10) Patent No.: US 9,176,032 B2
(45) Date of Patent: *Nov. 3, 2015

(54) METHODS OF ANALYZING AN H AND E STAINED BIOLOGICAL SAMPLE

(71) Applicant: General Electric Company, Schenectady, NY (US)

(72) Inventors: Anup Sood, Clifton Park, NY (US); Kevin Bernard Kenny, Niskayuna, NY (US); Arunkumar Natarajan, Niskayuna, NY (US); Lakshmi Sireesha Kaanumalle, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 201 days.

This patent is subject to a terminal disclaimer.

(21) Appl. No.: 13/786,747

(22) Filed: Mar. 6, 2013

(65) Prior Publication Data

US 2013/0178392 A1    Jul. 11, 2013

Related U.S. Application Data

(63) Continuation-in-part of application No. 13/336,409, filed on Dec. 23, 2011, now Pat. No. 8,568,991.

(51) Int. Cl.
| | |
|---|---|
| *G01N 33/53* | (2006.01) |
| *G01N 33/532* | (2006.01) |
| *G01N 33/533* | (2006.01) |
| *G01N 21/76* | (2006.01) |
| *G01N 1/30* | (2006.01) |
| *G01N 33/58* | (2006.01) |
| G01N 21/64 | (2006.01) |

(52) U.S. Cl.
CPC ................ *G01N 1/30* (2013.01); *G01N 33/582* (2013.01); *G01N 21/64* (2013.01); *G01N 21/6428* (2013.01)

(58) Field of Classification Search
CPC .. G01N 21/64; G01N 33/582; G01N 21/6428
See application file for complete search history.

(56) References Cited

U.S. PATENT DOCUMENTS

| | | | |
|---|---|---|---|
| 4,524,014 | A | 6/1985 | Finch et al. |
| 5,648,227 | A | 7/1997 | Basboll |
| 6,451,551 | B1 | 9/2002 | Zhan et al. |
| 6,627,177 | B2 | 9/2003 | Singaram et al. |
| 6,804,544 | B2 | 10/2004 | Van Antwerp et al. |
| 6,924,115 | B2 | 8/2005 | Schubert |
| 7,045,361 | B2 | 5/2006 | Heiss et al. |
| 7,329,505 | B2 | 2/2008 | Marmé |
| 7,629,125 | B2 | 12/2009 | Sood et al. |
| 7,714,303 | B2 | 5/2010 | Lundquist et al. |
| 7,741,045 | B2 | 6/2010 | Gerdes et al. |
| 7,741,046 | B2 | 6/2010 | Larsen et al. |
| 7,803,634 | B2 | 9/2010 | Klimov et al. |
| 7,919,254 | B2 | 4/2011 | Cohen et al. |
| 7,993,927 | B2 | 8/2011 | Frangioni |
| 8,036,462 | B2 | 10/2011 | Can et al. |
| 8,060,348 | B2 | 11/2011 | Cline et al. |
| 8,062,897 | B2 | 11/2011 | Capodieci et al. |
| 8,131,476 | B2 | 3/2012 | Cline et al. |
| 2002/0043651 | A1 | 4/2002 | Darrow et al. |
| 2006/0083688 | A1 | 4/2006 | Singaram et al. |
| 2008/0032321 | A1 | 2/2008 | Ginty et al. |
| 2008/0118944 | A1 | 5/2008 | Larsen et al. |
| 2009/0263612 | A1 | 10/2009 | Gascoyne et al. |
| 2010/0120043 | A1 | 5/2010 | Sood et al. |
| 2010/0216652 | A1 | 8/2010 | Eberwine et al. |
| 2011/0092381 | A1 | 4/2011 | Sood et al. |
| 2012/0112098 | A1 | 5/2012 | Hoyt |
| 2014/0024024 | A1 | 1/2014 | Sood et al. |

FOREIGN PATENT DOCUMENTS

| | | |
|---|---|---|
| CN | 1479870 A | 3/2004 |
| EP | 1234026 B1 | 8/2011 |
| WO | 2006132710 A1 | 12/2006 |
| WO | 2007136724 A2 | 11/2007 |
| WO | WO2008052338 A1 | 5/2008 |
| WO | 2008133729 A2 | 11/2008 |
| WO | 2011048184 A1 | 4/2011 |

OTHER PUBLICATIONS

Benharroch et al. ALK-positive Lymphoma: a single disease with a braod spectrum of morphology. Blood 1998, vol. 91, No. 6, pp. 2076-2084.*

International Search Report and Written Opinion from PCT Application No. PCT/US2012/067527 dated Feb. 8, 2013.

Benharroch, et al., "ALK-Positive Lymphoma: A Single Disease With a Broad Spectrum of Morphology", Blood-Journal of the American Society of Hematology, vol. 91, Issue 6, Mar. 15, 1998, pp. 2076-2084.

International Search Report and Written Opinion from PCT Application No. PCT/US2014/020659 dated Jun. 30, 2014.

Walgenbach-Bruenagel G., et al., "Detection of lymphatic invasion in early stage primary colorectal cancer with the monoclonal antibody D2-40", European Surgical Research, vol. 28, Aug. 15, 2006, pp. 438-444.

Helin H.O., et al. "Virtual Microscopy in Prostate Histopathology: Simultaneous Viewing of Biopsies Stained Sequentially with Hematoxylin and Eosin, and alpha-Methylacyl-Coenzyme a Racemase/p63 Immunohistochemistry", Journal of Urology, Baltimore, MD, Feb. 1, 2006, vol. 175, No. 2, pp. 495-499.

(Continued)

*Primary Examiner* — Shafiqul Haq
(74) *Attorney, Agent, or Firm* — Eileen B. Gallagher

(57) ABSTRACT

Methods comprising the use probing multiple targets in a H&E stained biological sample are provided. The methods include the steps of providing a hematoxylin and eosin stained biological sample containing multiple targets, observing the sample, removing the hematoxylin and partially removing the eosin by washing the sample, contacting the sample with a borate salt, and irradiating the sample to remove the residual eosin fluorescence. The method further includes the optionally performing the additional steps of binding at least one probe to one or more targets to the sample, observing a signal from the probe and contacting the sample with a bleaching agent. The process of binding, observing and bleaching may be iteratively repeated.

30 Claims, 10 Drawing Sheets

(56) References Cited

OTHER PUBLICATIONS

Tehmina, AZ, et al. "False positive labeling of prostate cancer with high molecular weight cyrokeratin: p63 a more specific immunomarker for basal cells", American Journal of Surgical Pathology, vol. 32, No. 12, Dec. 1, 2008, pp. 1890-1895.

Dardik, Michael, et al., "Efficacy of restaining prostate needle biopsies with high-molecular weigh cytokeratin," Human Pathology, vol. 31, No. 9, Sep. 1, 2000, pp. 115-1161.

Chen M., "Evaluation of applying Feulgen stain for DNA analysis on destained hematoxylin-eosin-stained cytologic smears", Analytical and Quantitative Cytology and Histology, vol. 26, No. 5, Oct. 1, 2004, pp. 255-258.

Chatterjee et al., "Photochemistry of Carbocyanine Alkyltriphenylborate Salts: Intra-Ion-Pair Electron Transfer and the Chemistry of Boranyl Radicals", J. Am. Chem. Society, No. 112, No. 17, pp. 6329-6338, 1990.

Paczkowski et al., "Polymethine Dyes as Fluorescent Probes and Visible-Light Photoinitiators for Free Radical Polymerization", Topics in Heterocyclic Chemistry, vol. 14, pp. 183-220, 2008.

Co-pending U.S. Appl. No. 13/551,190, filed Dec. 23, 2011, entitled Methods of Detecting DNA, RNA and Protein in Biological Samples.

European Search Report and Written Opinion issued from EP Application No. 12860159.8 dated Apr. 8, 2015.

Miller et al., "Photopolymerization Studies. III. Thermal Sensitization and Desensitization Effects", Macromolecules, vol. No. 7, Issue No. 2, pp. 179-187, 1974.

Eaton, "Dye-Sensitized Photopolymerization: Activation by Trialkylbenzylstannanes", Photographic Science and Engineering, vol. No. 23, pp. 150-154, 1979.

Eaton, "Electron Transfer Induced Photofragmentation as a Route to Free Radicals", Pure and Applied Chemistry, vol. No. 56, Issue No. 9, pp. 1191-1202, 1984.

Eaton, "Electron Transfer Processes in Imaging", Topics in Current Chemistry, vol. No. 156, pp. 199-225, 1990.

Borduchi et al., "A Simple Procedure for Rehybridization of Nuclei Analyzed Previously by Fish", Genetics and Molecular Biology, vol. No. 22, Issue No. 2, pp. 173-175, 1999.

Toth et al., "Simultaneous Visualization of Multiple Antigens with Tyramide Signal Amplification using Antibodies from the same Species", Journal of Histochemistry & Cytochemistry, vol. No. 55, Issue No. 6, pp. 545-554, 2007.

Zrazhevskiy et al., "Quantum Dot Imaging Platform for Single-Cell Molecular Profiling", Nature Communications, vol. No. 4, 2013.

Chinese Office Action issued in connection with corresponding Application No. 201280070449.4 on Jun. 24, 2015.

* cited by examiner

H & E Slide-
Brightfield

↓ AR

H & E Slide-
Brightfield

↕

Residual
Eosin
Fluorescence

Residual Eosin Fluorescence

| PICB

Autofluorescence after PICB

Control slide - No H & E

METHODS OF ANALYZING AN H AND E STAINED BIOLOGICAL SAMPLE

CROSS-REFERENCE TO RELATED APPLICATIONS

This application is a continuation in part of U.S. patent application Ser. No. 13/336,409 filed on Dec. 23, 2011 and is herein incorporated by reference.

BACKGROUND

Traditionally, hematoxylin and eosin staining (H&E) is one of the most common staining methods in histology. The morphology from the H&E is most widely used in medical diagnosis for cancer detection. However, increasingly molecular analysis of tissue by immunohistochemistry (IHC) or immunofluorescence (IF) and fluorescence in situ hybridization have become an essential part of cancer diagnosis in addition to morphological assessment. With great strides in targeted therapies, detailed molecular assessment of cancer tissue is fast becoming a requirement. Additionally with early cancer detection sample size is diminishing, making it difficult to perform various analyses required for complete characterization of disease.

While valuable, many of these current techniques may detect only a few targets at one time (such as IHC or fluorescence-based Western blots where number of targets detectable is limited by the fluorescence-based detection system) in a single sample. Further analysis of targets may require use of additional biological samples from the source, limiting the ability to determine relative characteristics of the targets such as the presence, absence, concentration, and/or the spatial distribution of multiple biological targets in the biological sample. Moreover, in certain instances, a limited amount of sample may be available for analysis or the individual sample may require further analysis.

Furthermore in many older cases only samples available are H&E stained slides and as patients are relapsing molecular analysis of this tissue can significantly benefit these patients by matching their disease to available targeted therapies. A major problem with using the previously H&E stained slide for IHC and FISH is the interference from H&E stains in both chromogenic detection in IHC and fluorescence detection for IF and FISH. Attempts have been made to remove H&E from tissue for interrogation. While this has allowed IHC with chromogen detection, IF and FISH are not feasible due to strong residual fluorescence from eosin. Removal of residual eosin fluorescence has not been feasible with many different techniques attempted to date.

For this reason, the general practice has been to use different tissue sections for H&E and molecular analysis. In rare cases where previously stained H&E slides are the only sample available, partial removal of H&E is performed and the slides are used for IHC using a chromogenic signal (Benharroch et. al. Blood 1998, 91:2076-2084) Thus there still remains a need for a method to remove H &E signals from the tissue and use the same tissue section for immunofluorescence and FISH.

BRIEF DESCRIPTION

Disclosed herein are novel methods probing multiple targets in a hematoxylin and eosin stained biological sample. In some embodiments, a method of probing multiple targets in a biological sample comprising a number of steps is disclosed. The steps include providing a hematoxylin and eosin stained biological sample containing multiple targets, observing the sample; removing the hematoxylin and partially removing the eosin by washing the sample, contacting the sample with an electron transfer reagent, and irradiating the sample to remove the residual eosin fluorescence.

In some embodiments, the photo-induced chemical bleaching agent is a borate salt. In some embodiments, the borate salt is represented by the following structural formula:

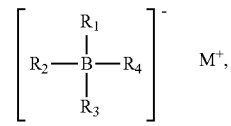

wherein:
each $R_1$, $R_2$, and $R_3$ is, independently, an alkyl, an alkenyl, an akynyl, an aryl or a heteroaryl, wherein said alkyl, alkenyl, alkynyl, aryl or heteroaryl is optionally substituted with one or more substituents selected from the group consisting of (C1-C4)alkyl, (C1-C4)alkoxy, (C1-C4)alkylamino, amino, hydroxyl, cyano, halogen, or nitro.

$R_4$ is an alkyl, an alkenyl, or an akynyl, wherein said alkyl, alkenyl, or alkynyl is optionally substituted with one or more substituents selected from the group consisting of (C1-C4)alkyl, aryl, (C1-C4)alkoxy, (C1-C4)alkylamino, amino, hydroxyl, cyano, halogen, or nitro, and $M^+$ is selected from the group consisting of organic and inorganic cations.

In still other embodiments, the method further comprises the additional steps of binding at least one probe to one or more targets to the sample, observing a signal from the probe bound in step, and optionally contacting the sample with a bleaching agent and repeating the binding step.

DETAILED DESCRIPTION

Figure 1:
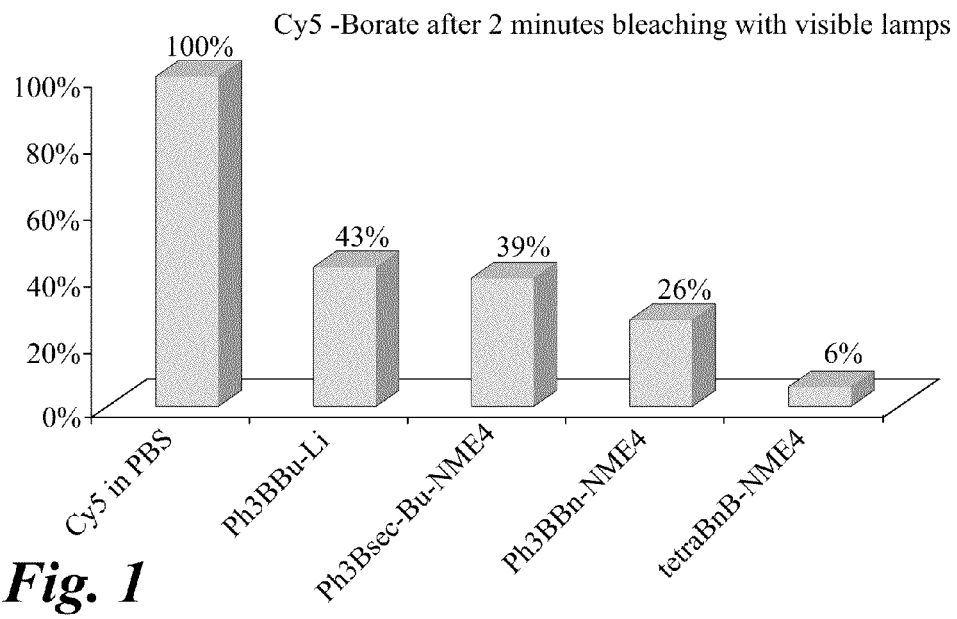
FIG. 1 is a standardized graph showing the percentage of signal intensity, compared to a control sample, after a two minute bleaching with a visible light source using the various borate salts.

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least each numerical parameter should at least be construed in light of the number of reported significant digits and by applying ordinary rounding techniques.

As used herein, the term "alkyl" refers to saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.). In certain embodiments, a straight chain or branched chain alkyl has 6 or fewer carbon atoms in its backbone (e.g., C1-C6 for straight chain, C3-C6 for branched chain) or 4 or fewer carbon atoms in its backbone (e.g., C1-C4 for straight chain, C3-C4 for branched chain). The term "C1-C6" alkyl refers to alkyl groups containing 1 to 6 carbon atoms. The term "C1-C4" alkyl refers to alkyl groups containing 1 to 4 carbon atoms. Moreover, the term alkyl includes both "unsubstituted alkyls" and "substituted alkyls," the latter of which refers to alkyl moieties having substituents replacing a hydrogen on one or more carbons of the hydrocarbon backbone. Such substituents can include, for example, (C1-C4)alkyl, (C1-C4)alkoxy, amino (including (C1-C4) alkylamino and (C1-C4)dialkylamino), aryls (including phenyl, naphthyl), cycloalkyls, hydroxyl, cyano, halogen, or nitro. Arylalkyls and cycloalkyls can be further substituted, e.g., with the substituents described above.

As used herein, the term "alkenyl" refers to unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups. Moreover, the term "alkenyl" includes both "unsubstituted alkenyls" and "substituted alkenyls," the latter of which refers to alkenyl moieties having substituents replacing a hydrogen on one or more carbons of the hydrocarbon backbone. Such substituents can include, for example, (C1-C4)alkyl, (C1-C4)alkoxy, aryls, amino (including (C1-C4)alkylamino and (C1-C4)dialkylamino), hydroxyl, cyano, halogen, or nitro.

As used herein, the term "alkynyl" refers to unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), or branched-chain alkynyl groups. Moreover, the term "alkynyl" includes both "unsubstituted alkynyls" and "substituted alkynyls," the latter of which refers to alkynyl moieties having substituents replacing a hydrogen on one or more carbons of the hydrocarbon backbone. Such substituents can include, for example, (C1-C4)alkyl, (C1-C4)alkoxy, aryls, amino (including (C1-C4)alkylamino and (C1-C4)dialkylamino), hydroxyl, cyano, halogen, or nitro.

As used herein, the term "alkoxy" refers to substituted and unsubstituted alkyl, alkenyl, and alkynyl groups covalently linked to an oxygen atom. Examples of alkoxy groups include, but are not limited to, methoxy, ethoxy, isopropyloxy, propoxy, butoxy, and pentoxy groups. In certain embodiments, a straight chain or branched chain alkoxy has 4 or fewer carbon atoms in its backbone (e.g., C1-C4 for straight chain, C3-C4 for branched chain). The term "C1-C4" alkyl refers to alkyl groups containing 1 to 4 carbon atoms.

As used herein, the term "amine" or "amino" refers to compounds or substituents where a nitrogen atom is covalently bonded to at least one carbon or heteroatom. The term includes "alkyl amino" which comprises groups and compounds wherein: the nitrogen is bound to at least one additional alkyl group. The term "dialkyl amino" includes groups wherein: the nitrogen atom is bound to at least two additional alkyl groups. In certain embodiments, these alkyl groups have 4 or fewer carbon atoms in their backbone (e.g., C1-C4 for straight chain, C3-C4 for branched chain). The term (C1-C4)alkylamino refers to groups and compounds, wherein the nitrogen is bound to at least one additional C1-C4 alkyl group. The term "(C1-C4)dialkylamino refers to groups and compounds, wherein the nitrogen is bound to at least two additional C1-C4 alkyl groups.

As used herein, the term "aryl" refers to groups, e.g., 5- and 6-membered single-ring aromatic groups, that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles," "heteroaryls" or "heteroaromatics." The aromatic ring can be substituted at one or more ring positions with such substituents as described above, as for example, (C1-C4) alkyl, (C1-C4) alkoxy, amino (including (C1-C4)alkylamino and (C1-C4)dialkylamino), hydroxyl, cyano, halogen, or nitro. Aryl groups can also be fused or bridged with alicyclic or heterocyclic rings which are not aromatic so as to form a polycycle (e.g., tetralin). The term heteroaryl includes unsaturated cyclic compounds such as azirine, oxirene, dithiete, pyrroline, pyrrole, furan, dihydrofuran, dihydrothiophene, thiophene, pyrazole, imidazole, oxazole, thiazole, isothiazole, 12,2,3-triazole, 1,2,4, triazole, dithiazole, tetrazole, pyridine, pyran, pyrimidine, pyran, thiapyrane, diazine, thiazine, dioxine, triazine and tetrazene.

As used herein, the term "antibody" refers to an immunoglobulin that specifically binds to and is thereby defined as complementary with a particular spatial and polar organization of another molecule. The antibody may be monoclonal or polyclonal and may be prepared by techniques that are well known in the art such as immunization of a host and collection of sera (polyclonal), or by preparing continuous hybrid cell lines and collecting the secreted protein (monoclonal), or by cloning and expressing nucleotide sequences or mutagenized versions thereof, coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM. Functional antibody fragments may include portions of an antibody capable of retaining binding at similar affinity to full-length antibody (for example, Fab, Fv and F(ab').sub.2, or Fab'). In addition, aggregates, polymers, and conjugates of immunoglobulins or their fragments may be used where appropriate so long as binding affinity for a particular molecule is substantially maintained.

As used herein, the term "binder" refers to a molecule that may bind to one or more targets in the biological sample. A binder may specifically bind to a target. Suitable binders may include one or more of natural or modified peptides, proteins (e.g., antibodies, affibodies, or aptamers), nucleic acids (e.g., polynucleotides, DNA, RNA, or aptamers); polysaccharides (e.g., lectins, sugars), lipids, enzymes, enzyme substrates or inhibitors, ligands, receptors, antigens, or haptens. A suitable binder may be selected depending on the sample to be analyzed and the targets available for detection. For example, a target in the sample may include a ligand and the binder may include a receptor or a target may include a receptor and the binder may include a ligand. Similarly, a target may include an antigen and the binder may include an antibody or antibody fragment or vice versa. In some embodiments, a target may include a nucleic acid and the binder may include a complementary nucleic acid. In some embodiments, both the target and the binder may include proteins capable of binding to each other.

As used herein, the term "biological sample" refers to a sample obtained from a biological subject, including sample of biological tissue or fluid origin obtained in vivo or in vitro. Such samples can be, but are not limited to, body fluid (e.g., blood, blood plasma, serum, or urine), organs, tissues, fractions, cells isolated from mammals including, humans and cell organelles. Biological samples also may include sections of the biological sample including tissues (e.g., sectional portions of an organ or tissue). Biological samples may also include extracts from a biological sample. Biological samples may comprise proteins, carbohydrates or nucleic acids.

A biological sample may be of prokaryotic origin, archaeal origin, or eukaryotic origin (e.g., insects, protozoa, birds, fish, and reptiles). In some embodiments, the biological sample is mammalian (e.g., rat, mouse, cow, dog, donkey, guinea pig, or rabbit). In certain embodiments, the biological sample is of primate origin (e.g., example, chimpanzee, or human).

As used herein, the term "control probe" refers to an agent having a binder coupled to a signal generator or a signal generator capable of staining directly, such that the signal generator retains at least 80 percent signal after contact with an electron transfer reagent and subsequent irradiation. A suitable signal generator in a control probe is not substantially inactivated, e.g., substantially bleached by photoactivated chemical bleaching, when contacted with the electron transfer reagent and irradiated. Suitable examples of signal generators may include a fluorophore that does not undergo bleaching under the conditions employed (e.g., DAPI).

As used herein, the term "enzyme" refers to a protein molecule that can catalyze a chemical reaction of a substrate. In some embodiments, a suitable enzyme catalyzes a chemical reaction of the substrate to form a reaction product that can bind to a receptor (e.g., phenolic groups) present in the sample. A receptor may be exogeneous (that is, a receptor extrinsically adhered to the sample or the solid-support) or endogeneous (receptors present intrinsically in the sample or the solid-support). Examples of suitable enzymes include peroxidases, oxidases, phosphatases, esterases, and glycosidases. Specific examples of suitable enzymes include horseradish peroxidase, alkaline phosphatase, β-D-galactosidase, lipase, and glucose oxidase.

As used herein, the term "enzyme substrate" refers to a chemical compound that is chemically catalyzed by an enzyme to form a reaction product. In some embodiments, the reaction product is capable of binding to a receptor present in the sample. In some embodiments, enzyme substrates employed in the methods herein may include non-chromogenic or non-chemiluminescent substrates. A signal generator may be attached to the enzyme substrate as a label.

As used herein, the term "electron transfer reagent" refers to a reagent that can engage in a photoreaction with a molecule capable of undergoing photoexcitation. This term also refers to a composition comprising a reagent that can engage in a photoreaction with a molecule capable of undergoing photoexcitation. In some embodiments, the molecule capable of undergoing photoexcitation may be a signal generator. In some embodiment, the electron transfer reagent may donate an electron to the signal generator in the course of a photoreaction. In alternative embodiments, the electron transfer reagent may accept an electron from the signal generator in the course of a photoreaction.

In some embodiments, the electron transfer reagent donating an electron to the signal generator in the course of a photoreaction may be a borate salt including the photo-induced chemical bleaching agent used in the invention for quenching eosin fluorescence. In alternative embodiments, the electron transfer reagent accepting an electron from the photoexcited molecule may be an onium salt [e.g., diphenyliodonium hexafluorophosphate (DPI) or dimethylphenacylsulfonium tetrafluoroborate (DMPS)], or tetrabutylammonium butyltriphenylborate (TBAB). An electron transfer reagent may include one or more chemicals that can engage in a photoreaction with a molecule capable of undergoing photoexcitation. The molecule capable of undergoing photoexcitation may be a signal generator. An electron transfer reagent may be contacted with the sample in the form of a solid, a solution, a gel, or a suspension. Other suitable electron transfer reagents may include sulfinates, enolates, carboxylates (e.g., ascorbic acid), organometallics and amines (e.g., triethanolamine, and N-phenylglycine). These and other electron transfer reagents have been previously described (see, e.g., Macromolecules 1974, 7, 179-187; Photogr. Sci. Eng. 1979, 23, 150-154; Topics in Current Chemistry, Mattay, J., Ed.; Springer-Verlag: Berlin, 1990, Vol. 156, pp 199-225; and Pure Appl. Chem. 1984, 56, 1191-1202.).

As used herein, the term "fluorophore" or "fluorescent signal generator" refers to a chemical compound, which when excited by exposure to a particular wavelength of light, emits light at a different wavelength. Fluorophores may be described in terms of their emission profile, or "color." Green fluorophores (for example Cy3, FITC, and Oregon Green) may be characterized by their emission at wavelengths generally in the range of 515-540 nanometers. Red fluorophores (for example Texas Red, CyS, and tetramethylrhodamine) may be characterized by their emission at wavelengths generally in the range of 590-690 nanometers. Examples of fluorophores include, but are not limited to, 4-acetamido-4'-isothiocyanatostilbene-2,2'disulfonic acid, acridine, derivatives of acridine and acridine isothiocyanate, 5-(2'-aminoethyl)amino naphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin, coumarin derivatives, 7-amino-4-methylcoumarin (AMC, Coumarin 120), 7-amino-trifluoromethylcouluarin (Coumaran 151), cyano sine; 4',6-diaminidino-2-phenylindole (DAPI), 5',5"-dibromopyrogallol-sulfonephthalein (Bromopyrogallol Red), 7-diethylamino-3-(4'-isothiocyanatophenyl)-4-methylcoumarin, -, 4,4'-diisothiocyanatodihydro-stilbene-2,2'-disulfonic acid, 4,4'-diisothiocyanato stilbene-2,2'-disulfonic acid, 5-[dimethylamino]naphthalene-1-sulfonyl chloride (DNS, dansyl chloride), fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein, fluorescein isothiocyanate (FITC), QFITC (XRITC); fluorescamine derivative (fluorescent upon reaction with amines); IR144; IR1446; Malachite Green isothiocyanate; 4-methylumbelliferone; ortho cresolphthalein; nitrotyrosine; pararosaniline; Phenol Red, B-phycoerythrin; o-phthaldialdehyde derivative (fluorescent upon reaction with amines); pyrene and derivatives such as pyrene, pyrene butyrate and succinimidyl 1-pyrene butyrate; Reactive Red 4 (Cibacron® Brilliant Red 3B-A), rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl Rhodamine, tetramethyl rhodamine isothiocyanate (TRITC); riboflavin; rosolic acid and lathanide chelate derivatives, cyanines, pyrelium dyes, squaraines, 1,3-dichloro-7-hydroxy-9,9-dimethyl-2(9H)-Acridinone (DDAO), and dimethylacridinone (DAO). In some embodiments, the fluorophore can be cyanine, rhodamine, BODIPY or 1,3-dichloro-7-hydroxy-9,9-dimethyl-2(9H)-Acridinone (DDAO) dyes. In a preferred embodiment, the fluorophore is a cyanine dye. In a further embodiment, the cyanine dye is Cy3 or Cy5.

As used herein the term "H&E stain" general refers to hematoxylin and eosin stain (H&E stain or HE stain). A histological section stained with H&E and is often termed "H&E section", "H+E section", or "HE section". The staining method involves application of hemalum, which is a complex formed from aluminum ions and oxidized haematoxylin. These colors nuclei of cells (and a few other objects, such as keratohyalin granules) blue. The nuclear staining is followed by counterstaining with an aqueous or alcoholic solution of eosin Y, which colors other, eosinophilic structures in various shades of red, pink and orange.

The staining of nuclei by hemalum does not require the presence of DNA and is probably due to binding of the dye-metal complex to arginine-rich basic nucleoproteins such as histones. The eosinophilic structures are generally composed of intracellular or extracellular protein. The Lewy bodies and Mallory bodies are examples of eosinophilic structures. Most of the cytoplasm is eosinophilic. Red blood cells are stained intensely red.

As used herein, the term "in situ" generally refers to an event occurring in the original location, for example, in intact organ or tissue or in a representative segment of an organ or tissue. In some embodiments, in situ analysis of targets may be performed on cells derived from a variety of sources, including an organism, an organ, tissue sample, or a cell culture. In situ analysis provides contextual information that may be lost when the target is removed from its site of origin. Accordingly, in situ analysis of targets describes analysis of target-bound probe located within a whole cell or a tissue sample, whether the cell membrane is fully intact or partially intact where target-bound probe remains within the cell. Furthermore, the methods disclosed herein may be employed to analyze targets in situ in cell or tissue samples that are fixed or unfixed.

As used herein, the terms "irradiation" or "irradiate" refer to act or process of exposing a sample or a solution to non-ionizing radiation. In some embodiments, the non-ionizing irradiation has wavelengths between 350 nm and 1.3 µm. In preferred embodiments, the non-ionizing radiation is visible light of 400-700 nm in wavelength. Irradiation may be accomplished by exposing a sample or a solution to a radiation source, e.g., a lamp, capable of emitting radiation of a certain wavelength or a range of wavelengths. In some embodiments, a molecule capable of undergoing photoexcitation is photoexcited as a result of irradiation. In some embodiments, the molecule capable of undergoing photoexcitation is a signal generator, e.g., a fluorescent signal generator. In some embodiments, irradiation of a fluorescent signal generator initiates a photoreaction between the fluorescent signal generator and the electron transfer reagent. In some embodiments, irradiation initiates a photoreaction substantially inactivates the signal generator by photoactivated chemical bleaching.

Optical filters may be used to restrict irradiation of a sample or a solution to a particular wavelength or a range of wavelengths. In some embodiments, the optical filters may be used to restrict irradiation to a narrow range of wavelengths for selective photoexcitation of one or more molecules capable of undergoing photoexcitation. The term "selective photoexcitation" refers to an act or a process, whereby one or more molecules capable of undergoing photoexcitation are photoexcited in the presence of one or more other molecules capable of undergoing photoexcitation that remain in the ground electronic state after irradiation.

In some embodiments, the molecule capable of undergoing photoexcitation is a fluorescent dye, e.g., a cyanine dye. In one further embodiment, irradiation limited to a range of wavelengths between 520-580 nm is used for selective photoexcitation of a Cy3 dye. In another further embodiment, irradiation limited to a range of wavelengths between 620-680 nm is used for selective photoexcitation of a Cy5 dye. In alternative embodiments, irradiation of a sample at a specific wavelength may also be accomplished by using a laser.

As used herein, the term "peroxidase" refers to an enzyme class that catalyzes an oxidation reaction of an enzyme substrate along with an electron donor. Examples of peroxidase enzymes include horseradish peroxidase, cytochrome C peroxidase, glutathione peroxidase, microperoxidase, myeloperoxidase, lactoperoxidase, or soybean peroxidase.

As used herein, the term "peroxidase substrate" refers to a chemical compound that is chemically catalyzed by peroxidase to form a reaction product. In some embodiments, peroxidase substrates employed in the methods herein may include non-chromogenic or non-chemiluminescent substrates. A fluorescent signal generator may be attached to the peroxidase substrate as a label.

As used herein, the term "bleaching", "photoactivated chemical bleaching" or "photoinduced chemical bleaching" refers to an act or a process whereby a signal generated by a signal generator is modified in the course of a photoreaction. In certain embodiments, the signal generator is irreversibly modified.

In some embodiments, the signal is diminished or eliminated as a result of photoactivated chemical bleaching. In some embodiments, the signal generator is completely bleached, i.e., the signal intensity decreases by about 100%. In some embodiments, the signal is an optical signal, and the signal generator is an optical signal generator. The term "photoactivated chemical bleaching" is meant to exclude photobleaching, or loss of signal (e.g., fluorescent signal) that may occur in the absence of electron transfer reagent, e.g., after continued irradiation of a signal generator, such as a fluorophore, or after its continued exposure to light.

As used herein, the term "photoexcitation" refers to an act or a process whereby a molecule transitions from a ground electronic state to an excited electronic state upon absorption of radiation energy, e.g. upon irradiation. Photoexcited molecules can participate in chemical reactions, e.g., in electron transfer reactions. In some embodiments, a molecule capable of undergoing photoexcitation is a signal generator, e.g., a fluorescent signal generator.

As used herein, the term "photoreaction" or a "photoinduced reaction" refers to a chemical reaction that is initiated and/or proceeds as a result of photoexcitation of at least one reactant. The reactants in a photoreaction may be an electron transfer reagent and a molecule capable of undergoing photoexcitation. In some embodiments, a photoreaction may involve an electron transfer from the electron transfer reagent to the molecule that has undergone photoexcitation, i.e., the photoexcited molecule. In alternative embodiments, a photoreaction may also involve an electron transfer from the molecule that has undergone photoexcitation to the electron transfer reagent. In some embodiments, the molecule capable of undergoing photoexcitation is a fluorescent signal generator, e.g., a fluorophore. In some embodiments, photoreaction results in irreversible modification of one or more components of the photoreaction. In some embodiments, photoreaction substantially inactivates the signal generator by photo activated chemical bleaching.

In some embodiments, the photoreaction may involve in intermolecular electron transfer between the electron transfer reagent and the photoexcited molecule, e.g., the electron transfer occurs when the linkage between the electron transfer reagent and the photoexcited molecule is transitory, forming just prior to the electron transfer and disconnecting after electron transfer.

In some embodiments, the photoreaction may involve intramolecular electron transfer between the electron transfer reagent and the photoexcited molecule, e.g. the electron transfer occurs when the electron transfer reagent and the photoexcited molecule have been linked together, e.g., by covalent or electrostatic interactions, prior to initiation of the electron transfer process. The photoreaction involving the intramolecular electron transfer can occur, e.g., when the molecule capable of undergoing photoexcitation and the electron transfer reagent carry opposite charges and form a complex held by electrostatic interactions. For example, a cationic dye, e.g., a cationic cyanine dye and triphenylbutyl borate anion may form a complex, wherein intramolecular electron transfer may occur between the cyanine and borate moieties upon irradiation.

As used herein, the term "probe" refers to an agent having a binder and a label, such as a signal generator or an enzyme. In some embodiments, the binder and the label (signal generator or the enzyme) are embodied in a single entity. The binder and the label may be attached directly (e.g., via a fluorescent molecule incorporated into the binder) or indirectly (e.g., through a linker) and applied to the biological sample in a single step. In alternative embodiments, the binder and the label are embodied in discrete entities (e.g., a primary antibody capable of binding a target and an enzyme or a signal generator-labeled secondary antibody capable of binding the primary antibody). When the binder and the label (signal generator or the enzyme) are separate entities they may be applied to a biological sample in a single step or multiple steps. As used herein, the term "fluorescent probe" refers to an agent having a binder coupled to a fluorescent signal generator. In some embodiments, the probe may comprise an optical signal generator, such that the signal observed is an optical signal. In some embodiments, the probe may comprise a fluorescent signal generator, such that the signal observed is a fluorescent signal.

As used herein, the term "signal generator" refers to a molecule capable of providing a detectable signal using one or more detection techniques (e.g., spectrometry, calorimetry, spectroscopy, or visual inspection). Suitable examples of a detectable signal may include an optical signal, and electrical signal. Examples of signal generators include one or more of a chromophore, a fluorophore, or a Raman-active tag. As stated above, with regard to the probe, the signal generator and the binder may be present in a single entity (e.g., a target binding protein with a fluorescent label) in some embodiments. Alternatively, the binder and the signal generator may be discrete entities (e.g., a receptor protein and a labeled-antibody against that particular receptor protein) that associate with each other before or upon introduction to the sample.

In some embodiments, the signal generator may be an optical signal generator. In some embodiments, the optical signal generator may be a fluorescent signal generator, e.g., a fluorophore. In preferred embodiments, the fluorescent signal generator may be a cyanine dye, e.g., Cy3, Cy5 or Cy7. In some embodiments, the signal generator, e.g., a fluorophore, may be charged. In one embodiment, the signal generator is a cationic fluorescent dye.

As used herein, the term "solid support" refers to an article on which targets present in the biological sample may be immobilized and subsequently detected by the methods disclosed herein. Targets may be immobilized on the solid support by physical adsorption, by covalent bond formation, or by combinations thereof. A solid support may include a polymeric, a glass, or a metallic material. Examples of solid supports include a membrane, a microtiter plate, a bead, a filter, a test strip, a slide, a cover slip, and a test tube.

As used herein, the term "specific binding" refers to the specific recognition of one of two different molecules for the other compared to substantially less recognition of other molecules. The molecules may have areas on their surfaces or in cavities giving rise to specific recognition between the two molecules arising from one or more of electrostatic interactions, hydrogen bonding, or hydrophobic interactions. Specific binding examples include, but are not limited to, antibody-antigen interactions, enzyme-substrate interactions, polynucleotide interactions, and the like. In some embodiments, a binder molecule may have an intrinsic equilibrium association constant (KA) for the target no lower than about 105 M-1 under ambient conditions such as a pH of about 6 to about 8 and temperature ranging from about 0° C. to about 37° C.

As used herein, the term "target" refers to the component of a biological sample that may be detected when present in the biological sample. The target may be any substance for which there exists a naturally occurring specific binder (e.g., an antibody), or for which a specific binder may be prepared (e.g., a small molecule binder or an aptamer). In general, a binder may bind to a target through one or more discrete chemical moieties of the target or a three-dimensional structural component of the target (e.g., 3D structures resulting from peptide folding). The target may include one or more of natural or modified peptides, proteins (e.g., antibodies, affibodies, or aptamers), nucleic acids (e.g., polynucleotides, DNA, RNA, or aptamers); polysaccharides (e.g., lectins or sugars), lipids, enzymes, enzyme substrates, ligands, receptors, antigens, or haptens. In some embodiments, targets may include proteins or nucleic acids.

The disclosed methods relate generally to detection of multiple targets in a single biological sample which is subjected to Hematoxylin and eosin stain (H&E) at some time during its analysis and allows for removal of the H&E signals from the tissue. The same tissue may then be subjected to immunofluorescence and FISH staining. In some embodiments, methods of detecting multiple targets in a single H&E stained biological sample using the same detection channel are disclosed. The invention includes embodiments that relate to methods applicable in analytical, diagnostic, or prognostic applications such as analyte detection, fluorescence-activated cell sorting (FACS), histochemistry, immunohistochemistry, or immunofluorescence. In some embodiments, the methods disclosed herein may be particularly applicable in histochemistry, immuno staining, immunohistochemistry, immunoassays, immunofluorescence or fluorescence in situ hybridization.

In some embodiments, the method disclosed comprises a two-step protocol wherein in the first step hematoxylin and a majority of the eosin is removed from the H&E stained sample by different washing protocols. In a second step, irreversible quenching of residual eosin fluorescence by photo-induced electron transfer based chemistry, herein referred to as Photoinduced Chemical Bleaching (PICB), and is then applied to remove the residual eosin signal. This PICB process involves excitation of eosin in the presence of an electron donor or acceptor. Following excitation an electron is transferred between the dye and either the donor or the acceptor and the resultant reactive dye undergoes further reaction or rearrangements with an accompanied change in optical properties. For example, a biological sample is stained with eosin. After imaging, the slide is flooded with a borate salt buffer and light from mercury, halogen or xenon lamp, an LED or another light source is shined on the tissue to bleach the eosin signal. After signal bleaching, the biological sample is available for further molecular analysis either by IHC, IF or FISH.

While not definitive, the mechanism of eosin bleaching may be based on electron transfer from borate to the eosin molecule after the photoexcitation of the eosin followed by generation of an alkyl radical from borate radical degradation. Subsequent reaction of the dye with the alkyl radical or other species in the buffer may then destroy the dye signal. In some embodiments, the photoreaction comprises intermolecular electron transfer. In other embodiments, the photoreaction comprises intramolecular electron transfer.

In some embodiments, the eosin signal is irreversibly modified. In some embodiments, the eosin signal is irreversibly modified by a photoreaction that inactivates the signal generator by photoactivated chemical bleaching.

In some embodiments, electron transfer agent which undergoes photo induced chemical bleaching agent (PICB) is a borate salt. In some embodiments, the borate salt is represented by the following structural formula:

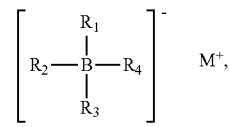

wherein:

each R1, R2, and R3 is, independently, an alkyl, an alkenyl, an akynyl, an aryl or a heteroaryl, wherein said alkyl, alkenyl, alkynyl, aryl or heteroaryl is optionally substituted with one or more substituents selected from the group consisting of (C1-C4)alkyl, (C1-C4)alkoxy, (C1-C4)alkylamino, amino, hydroxyl, cyano, halogen, or nitro;

R4 is an alkyl, an alkenyl, or an akynyl, wherein said alkyl, alkenyl, or alkynyl is optionally substituted with one or more substituents selected from the group consisting of (C1-C4)alkyl, (C1-C4)alkoxy, aryl, (C1-C4)alkylamino, amino, hydroxyl, cyano, halogen, or nitro; and M+ is selected from the group consisting of organic and inorganic cations.

In some embodiments, each R1, R2, and R3 is aryl. In some embodiments, said aryl is phenyl. In some embodiments, said phenyl is an unsubstituted phenyl.

In some embodiments, R4 is an optionally substituted alkyl. In some embodiments, R4 is butyl or benzyl.

In some embodiments, each R1, R2, and R3 is an optionally substituted aryl and R4 is an optionally substituted alkyl. In a further embodiment, each R1, R2, and R3 is phenyl and R4 is butyl or benzyl, and the borate salt is triphenylbutyl borate salt or triphenylbenzyl borate salt.

In some embodiments, M+ is an inorganic cation. In some embodiments, the inorganic cation is Li+, Na+ or K+.

The following structures are non-limiting examples of borate salts useful in the invention a PICB agents:

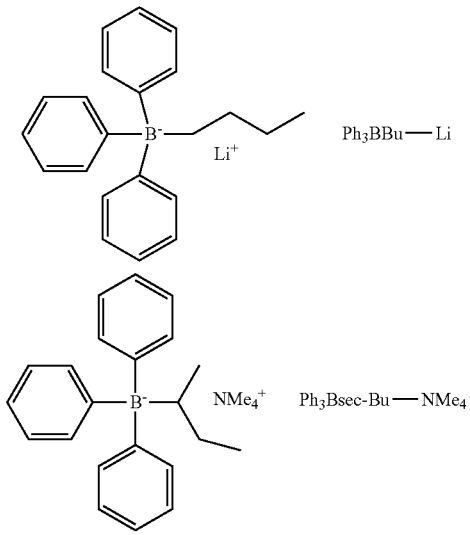

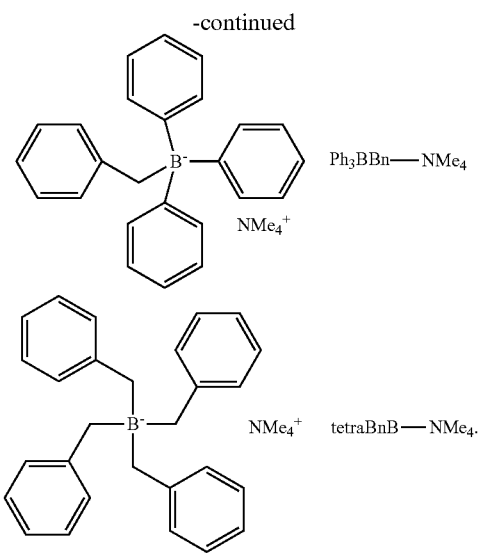

Ph₃BBn——NMe₄ tetraBnB——NMe₄.

In some embodiments, the PICB agent may be in the form of a solution. In one embodiment, the PICB agent is present in the form of a buffered aqueous solution. In some embodiments, the electron transfer reagent may be a borate salt. In further embodiments, the PICB agent may be a triphenyl butyl borate salt present at a concentration of 0.001 mM to 1000 mM. In a preferred embodiment, the concentration of triphenyl butyl borate is from 20 mM to 100 mM. In certain embodiments, the PICB agent may be a triphenyl benzyl borate present at a concentration of 0.001 mM to 10 mM and more preferably at a concentration of 200 uM to 10 mM.

Irradiation of the sample contacted with the PICB agent may be carried out for a predetermined amount of time. The duration of irradiation may depend on the desired duration of the photoreaction between the PICB agent and the eosin stain. In some embodiments, the irradiation step may be performed for about 20 seconds to about 60 minutes, preferably for about 20 seconds to about 15 minutes, and even more preferably, for about 20 seconds to about 5 minutes. In some embodiments, the irradiation step may be performed until no residual signal is observed from the eosin stain. In some embodiments, the irradiation step may be performed at room temperature.

In some embodiments, the photoreaction is carried out at a temperature of 4-50° C., more preferably, at a temperature of 20-30° C.

In some embodiments, the photoreaction is carried out in a solution. In some embodiments, the solution is a buffered solution. In a further embodiment, the buffered solution is the solution buffered in phosphate buffered saline (PBS). In some embodiments, the solution is buffered at pH of 5-9. In a preferred embodiment, the pH of the solution is 6-8.

In some embodiments, a characteristic of the eosin signal may be observed after the photoreaction to determine the effectiveness of the bleaching. For example, a color may be observed before the photoreaction and the color may be absent after the photoreaction. In some embodiments, a decrease in signal intensity by a predetermined amount may be referred to as signal modification, or photoactivated chemical bleaching, or bleaching. In some embodiments, modification of the signal or photoactivated chemical bleaching, may refer to a decrease in the signal intensity by an amount in a range of greater than about 50 percent. In some embodiments, modification of the signal or photoactivated chemical bleaching, may refer to a decrease in the signal intensity by an amount in a range of greater than about 60 percent. In some embodiments, modification of the signal or photoactivated chemical bleaching, may refer to a decrease in the signal intensity by an amount in a range of greater than about 80 percent. In some embodiments, modification of the signal or photoactivated chemical bleaching, may refer to a decrease in the signal intensity by an amount in a range of greater than about 90 percent. In some embodiments, modification of the signal or photoactivated chemical bleaching, may refer to a decrease in the signal intensity by an amount in a range of greater than about 95 percent. In some embodiments, modification of the signal, or photoactivated chemical bleaching, may refer to a decrease in the signal intensity by an amount in a range of about 100 percent, or to complete bleaching.

Figure 2:
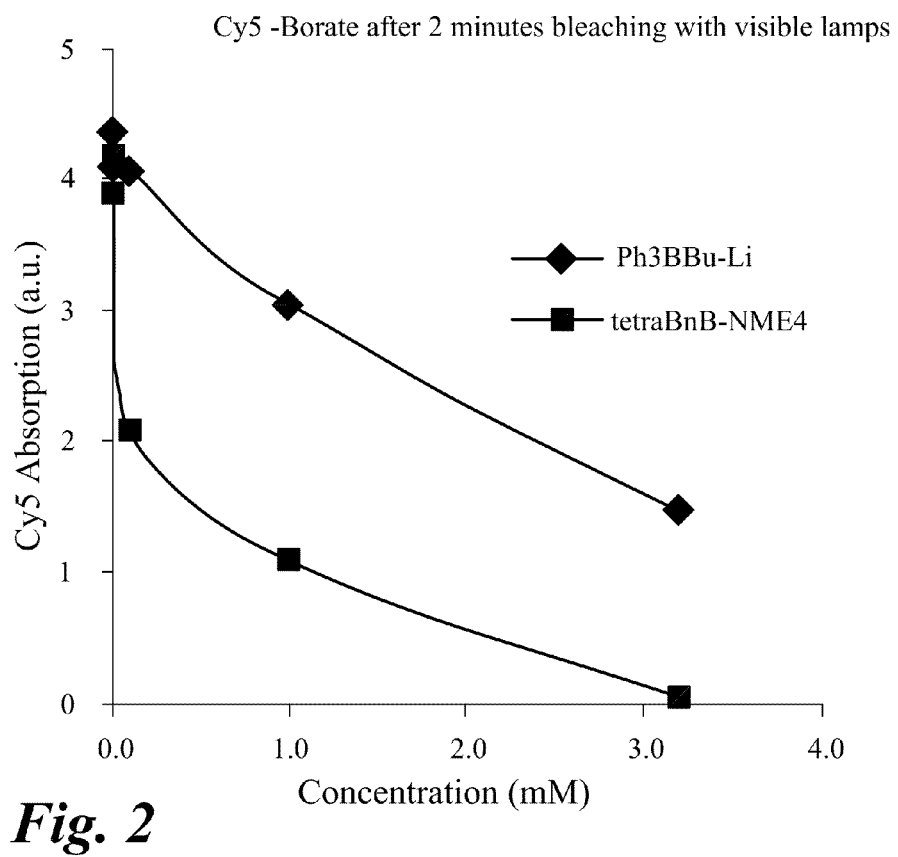
FIG. 2 is a graphical representation of the effect of borate concentration after two minutes of bleaching with a visible light source.

Results of photobleaching of representative borate salts are shown graphically in FIG. 1 and FIG. 2. FIG. 1 is a standardized graph showing the percentage of signal intensity, compared to a control sample, after a two minute bleaching with a visible light source using the various borate salts. FIG. 2 is a graphical representation of the effect of borate concentration after two minutes of bleaching with visible light sources. As shown concentration of the two borate salts were varied (0 to 3.25 mM). The decay in Cy5 intensity is shown as concentration increases.

As such, in some embodiments, the methods disclosed herein may be employed in a process where the H&E stained sample, after undergoing PICB may then be subjected to additional immunostaining procedures. For instance, the additional immunostainng procedures available after the H&E stained sample has undergone PICB may allow detection of a plurality of targets in the same biological sample with little or no effect on the integrity of the biological sample. Detecting the targets in the same biological sample may further provide spatial information about the targets in the biological sample. Methods disclosed herein may also be applicable in analytical applications where a limited amount of biological sample may be available for analysis and the same sample may have to be processed for multiple analyses. Methods disclosed herein may also facilitate multiple analyses of solid-state samples (e.g., tissue sections) or samples adhered to a solid support without substantially stripping the probes and the targets.

Furthermore, the same detection channel may be employed for detection of different targets in the sample, enabling fewer chemistry requirements for analyses of multiple targets. The methods may further facilitate analyses based on detection methods that may be limited in the number of simultaneously detectable targets because of limitations of resolvable signals. For example, using fluorescent-based detection, the number of targets that may be simultaneously detected may be limited to about four as only about four fluorescent signals may be resolvable based on their excitation and emission wavelength properties. In some embodiments, the methods disclosed herein may allow detection of greater than four targets using fluorescent-based detection system.

Methods of iteratively analyzing an individual sample have been described in U.S. Pat. No. 7,629,125 and U.S. Pat. No. 7,741,046. In particular, U.S. Pat. No. 7,741,046 provides methods of detecting multiple targets in a biological sample that involve the use of oxidation for inactivating signal generators (e.g., for bleaching fluorescent dyes.) The oxidation reaction is accomplished by using oxidizing reagents, such as hydrogen peroxide as well as photoxidation and which are herein incorporated by reference.

In still other methods, the methods employ, e.g., a signal cycling process wherein in each cycle, a photoreaction step allows the same signal generators, e.g., fluorophores, to be reused in the subsequent cycle to detect additional markers, e.g., proteins. These methods can be employed, e.g., for sequentially analyzing a biological sample to discern, among other things, the presence, absence, concentration, and/or spatial distribution of multiple biological targets in a biological sample. The photoreaction step can include applying an electron transfer agent, e.g., a borate salt, and initiating a photoreaction, e.g., by irradiating the sample with visible light, to inactivate the signal generator, e.g., fluorescent dye.

Figure 3A:
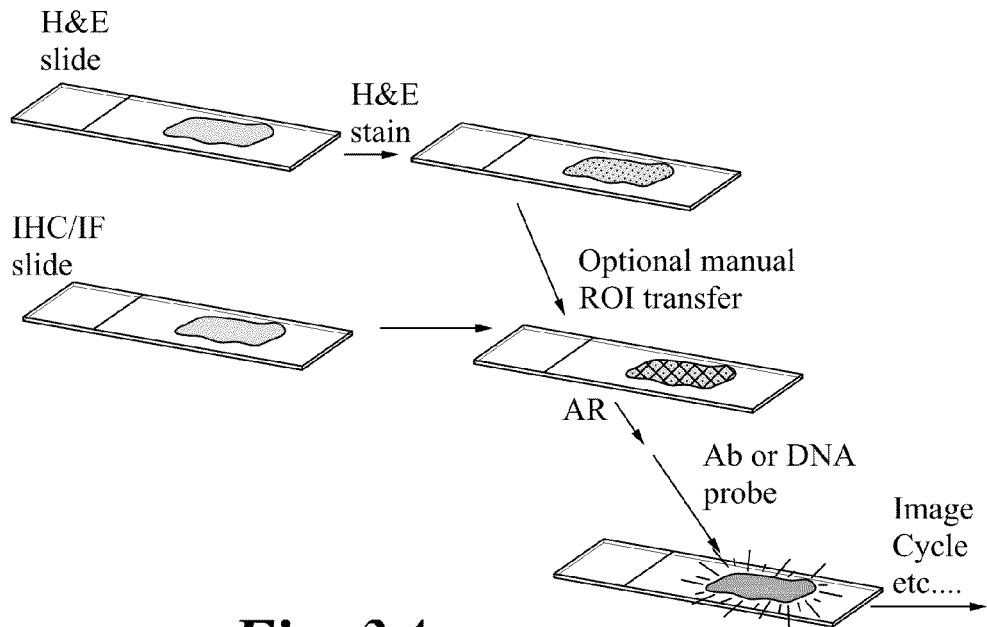
FIG. 3 is an illustrated example of a current approach to H&E and IHC or IF imaging using two slides (FIG. 3A) compared to single slide approach using PICB to remove eosin staining (FIG. 3b).

Process improvement afforded by the invention is illustrated in FIG. 3. FIG. 3A is a representation of a current approach wherein two separate slides are processed for H&E and IHC, IF or FISH. In some instances, an H&E slide is initially processed and stained to identify a region of interest (ROI). A second slide, which may be part of a serial tissue section is then processed, for example using IHC or FISH, using the information obtained from the H&E staining of the first slide.

Figure 3B:
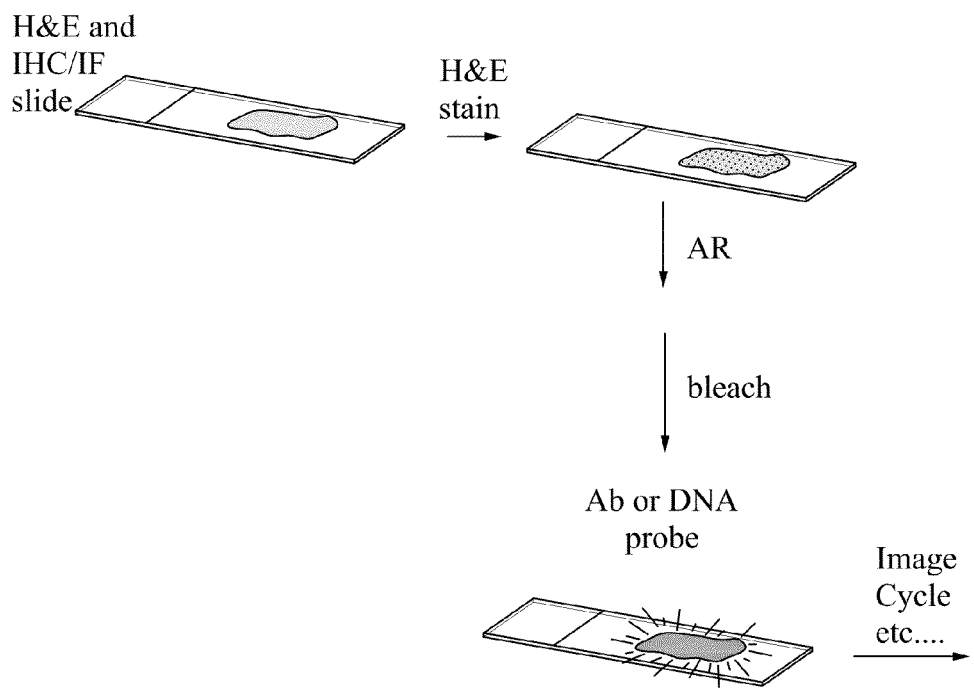

An improvement to the method is shown in one embodiment as illustrated in FIG. 3B. As shown, a single slide is capable of combining both H&E and IHC, IF or FISH staining. The slide is subjected to the H&E staining and undergoes PICB. The same slide is then subjected to IHC, IF or FISH protocol. The process allows information on single slide and replaces the need for ROI transfer time, which may be in the range of 2 or more hours, to be processed with less than 0.5 hours of H&E removal. In addition to the time savings, the process also saves tissue and reduces error in that morphological and molecular information is now obtainable from the same section.

In addition to improvements in process time and tissue retention, in some embodiments the method also allows for the removal of eosin fluorescence by PICB such that the residual eosin fluorescence does not interfere with subsequent imaging.

Figure 4:
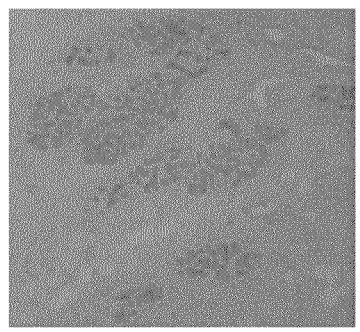
FIG. 4 shows residual eosin fluorescence (bottom image) after H&E removal by conventional methods while brightfield image in the middle appears to show complete removal of hematoxylin and eosin.
Figure 4:
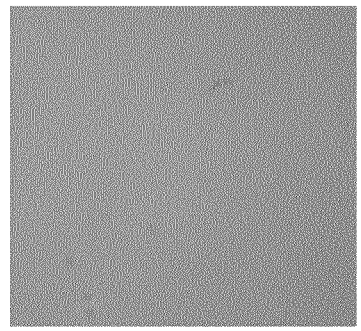
Figure 4:
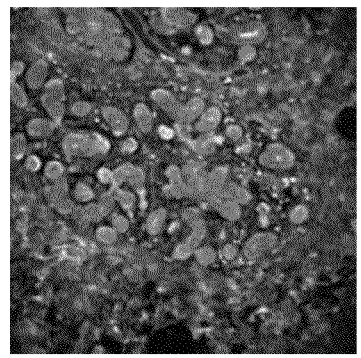

As shown in FIG. 4 removal of H&E by conventional methods while appears to remove both hemotoxylin and eosin as shown in brightfield image (middle image), fluorescence imaging show significant residual eosin fluorescence (bottom image) that can interfere with subsequent fluorescence based detection.

Figure 5:
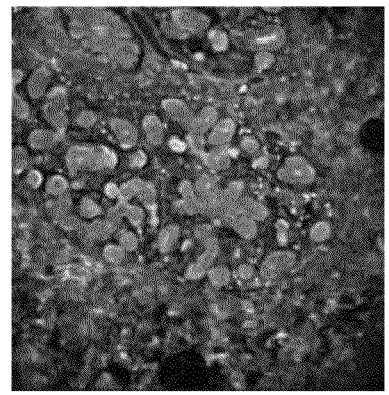
FIG. 5 shows almost complete removal of residual eosin fluorescence by photo-induced chemical bleaching.
Figure 5:
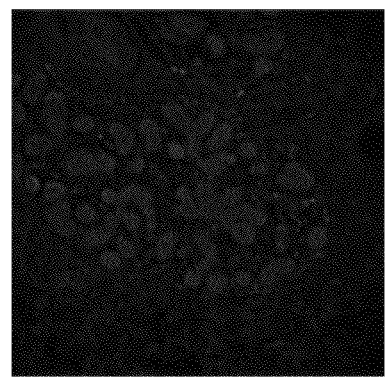
Figure 5:
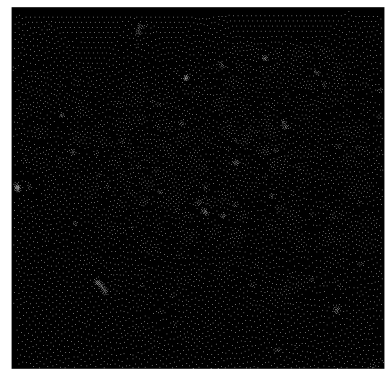

FIG. 5 shows the same region of interest (ROI) whereby the residual eosin fluorescence is removed by PICB treatment. The eosin fluorescence is significantly reduced (middle image) and is comparable to the autofluorescence in the control slide which was not subjected to H&E staining (bottom image).

Figure 6:
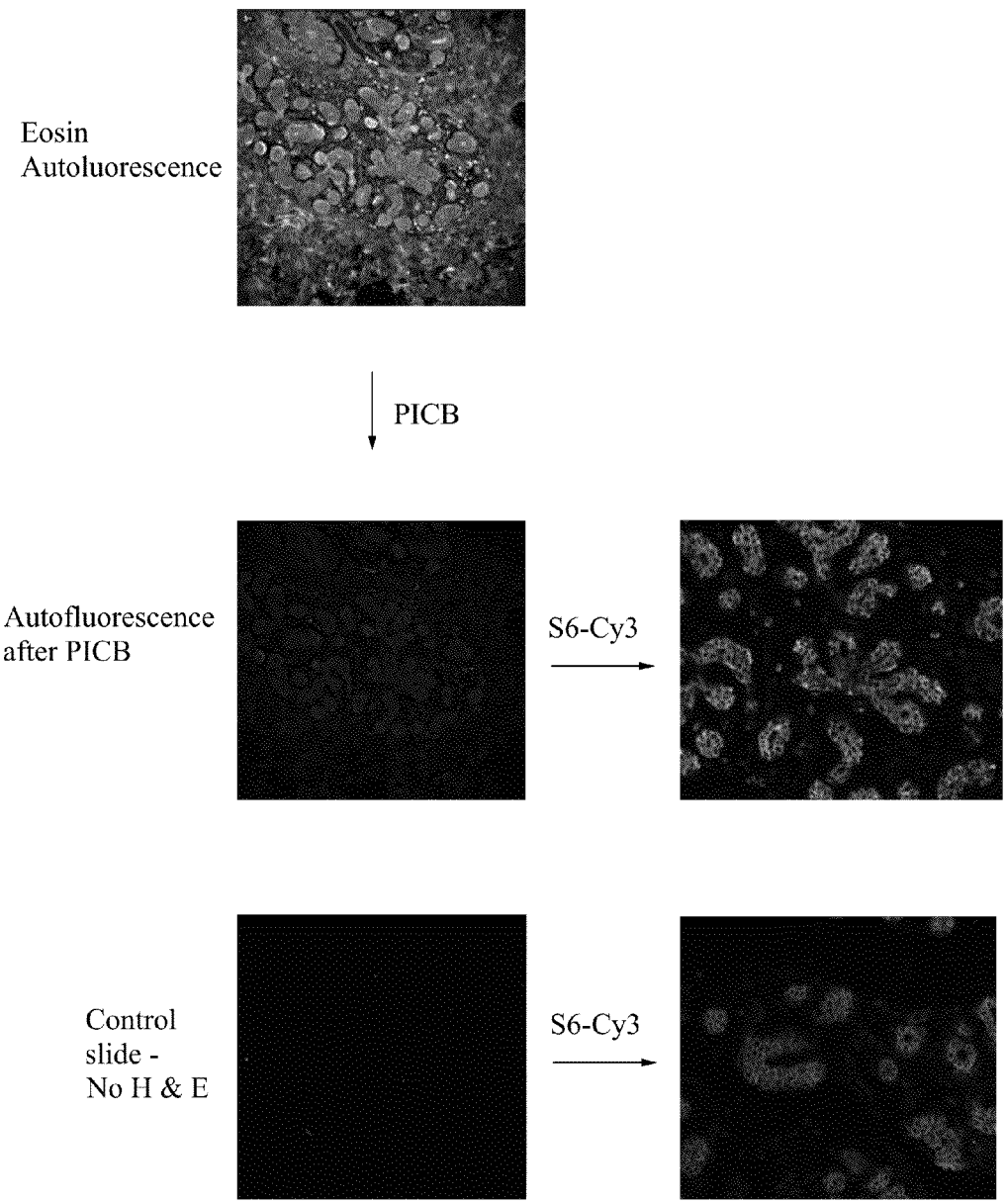
FIG. 6 shows immunofluorescence staining of a PICB bleached H&E slide is comparable to immuno staining on a control slide that was not subjected to H&E staining.

Subsequent staining of the slide with Cy3-labeled antibody targeting S6 protein (FIG. 6) shows specific staining of protein (middle panel, left image—after eosin fluorescence removal by PICB, right S6 stained image after PICB) that is easily discernible and is comparable to signal observed on the controlled slide (bottom panel, left image-tissue autofluorescence of a slide that was not subjected to H&E, right image, S6 stained image).

In some embodiments, the method allows for H&E staining, the removal of the H&E staining comprising in part the removal of eosin fluorescence by PICB, and subsequent high throughput multiplexing biological sample analysis that includes a signal cycling process, wherein in each cycle, staining and imaging is followed by applying an electron transfer reagent and irradiation of the biological sample. The method allows rapid signal cycling without significantly modifying the components of the biological sample that are different from the probe.

Figure 7:
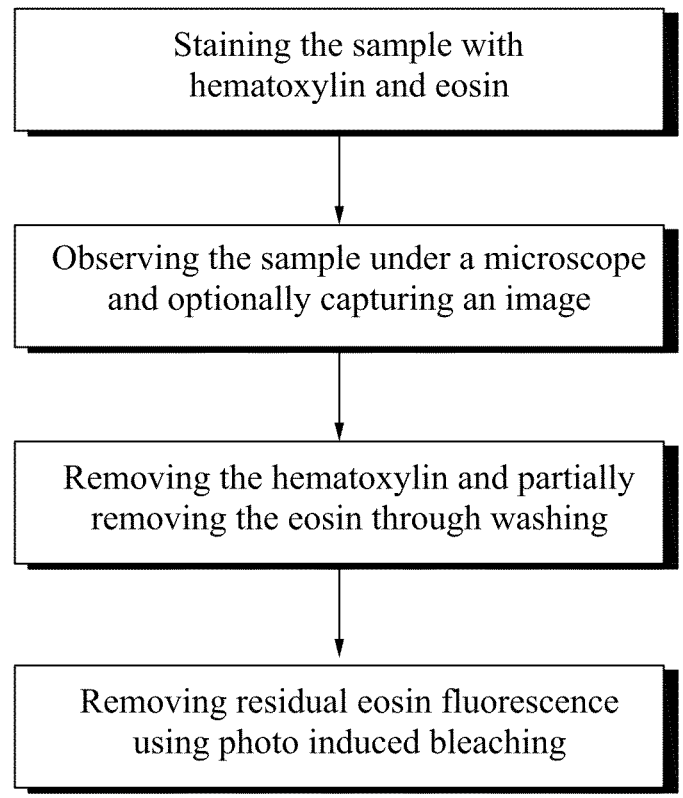
FIG. 7 is a flow chart of steps involved in the process of using a slide for H&E and removing the H&E signal so the slide can be subsequently used for other analysis.

FIG. 7 is a flow chart representing one embodiment of the invention. As shown, the method comprises providing a biological sample and:

(a) staining the biological sample with hematoxylin and eosin (b) observing the sample under a microscope and optionally capturing an image (c) removing the hematoxylin and partially removing the eosin through washing (d) removing residual eosin fluorescence using photo induced chemical bleaching.

In still other embodiments, the methods may further comprise the step of antigen retrieval (AR) after the H&E staining protocol. The antigens, those exposed may then be subjected to PICB and immunohistochemical staining, such as IF. This is further illustrated in FIG. 8-10.

Generally an antigen target may be present on the surface of a biological sample (for example, an antigen on a surface of a tissue section). In some embodiments, an antigen target may not be inherently present on the surface of a biological sample and the biological sample may have to be processed to make the target available on the surface (e.g., antigen recovery, enzymatic digestion or epitope retrieval). An antigen retrieval step may be performed as such involving high temperature heating in acid and or base. Such procedures are further described in U.S. patent application Ser. No. 13/551190 filed Jul. 17, 2012 herein incorporated by reference.

Figure 8:
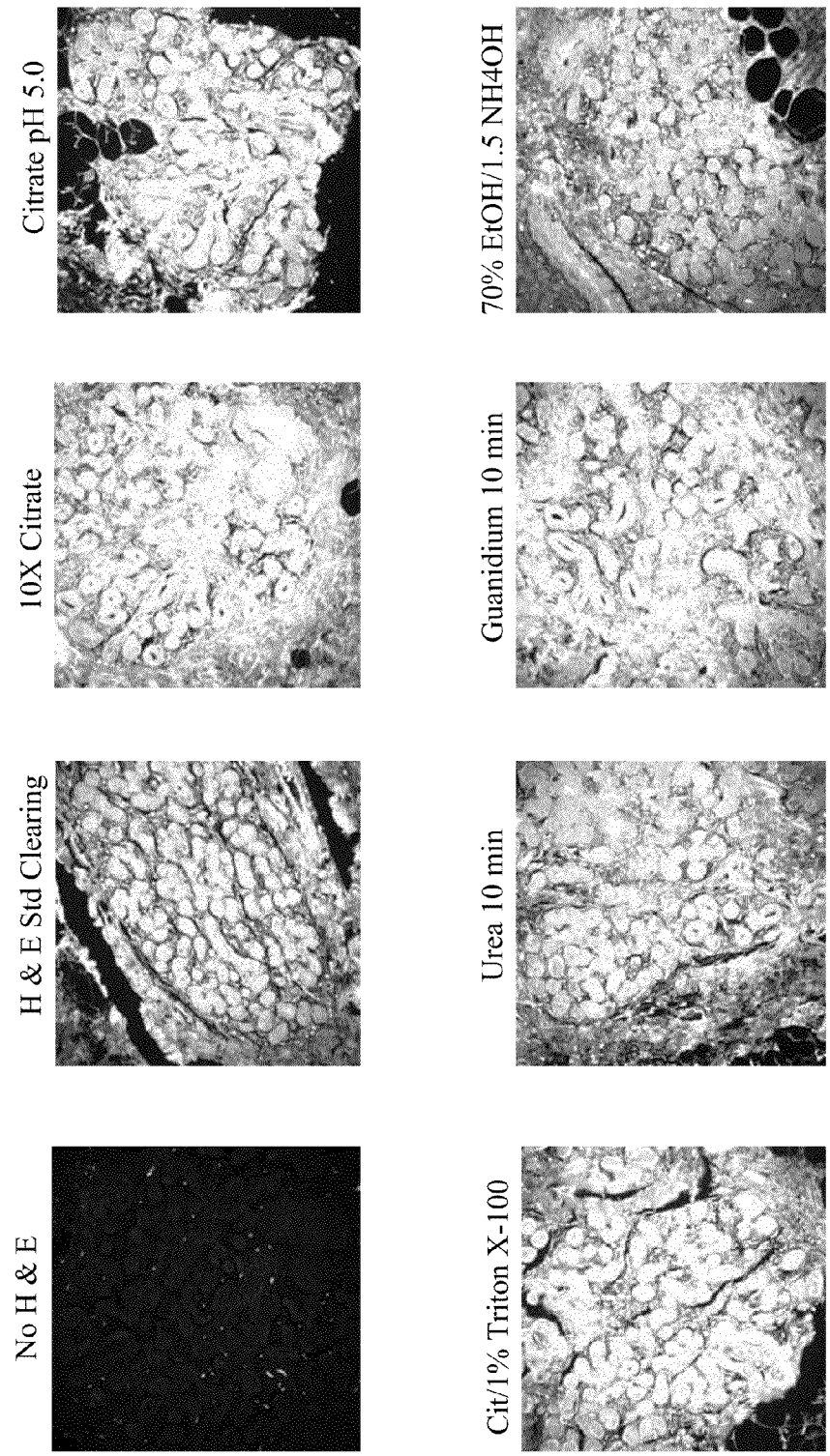
FIG. 8 shows various failed attempts to remove eosin fluorescence using buffers/salts, detergents, denaturants and solvents.
Figure 9:
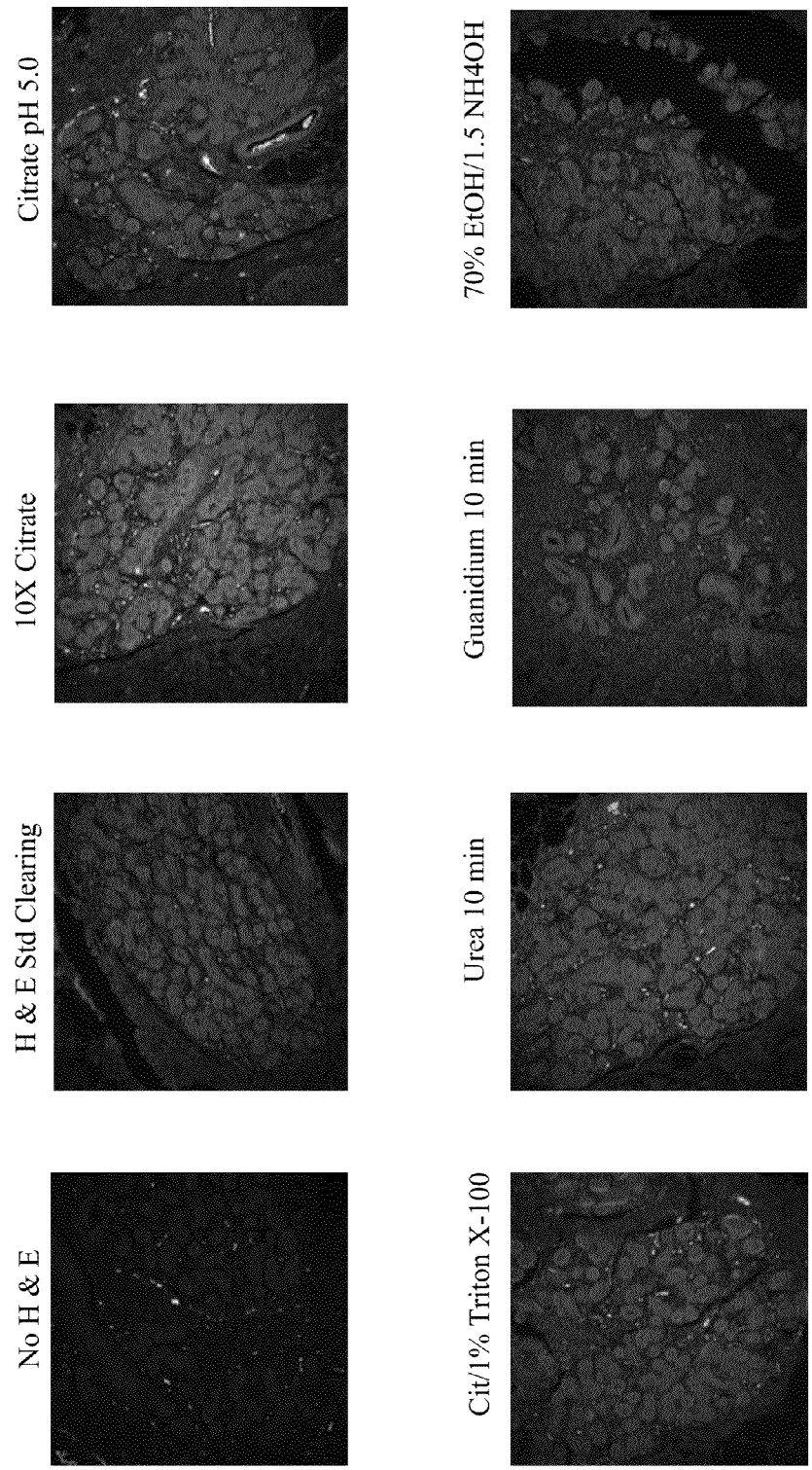
FIG. 9 shows almost complete removal of eosin fluorescence with PICB of slides subjected to various treatments shown in FIG. 8.
Figure 10:
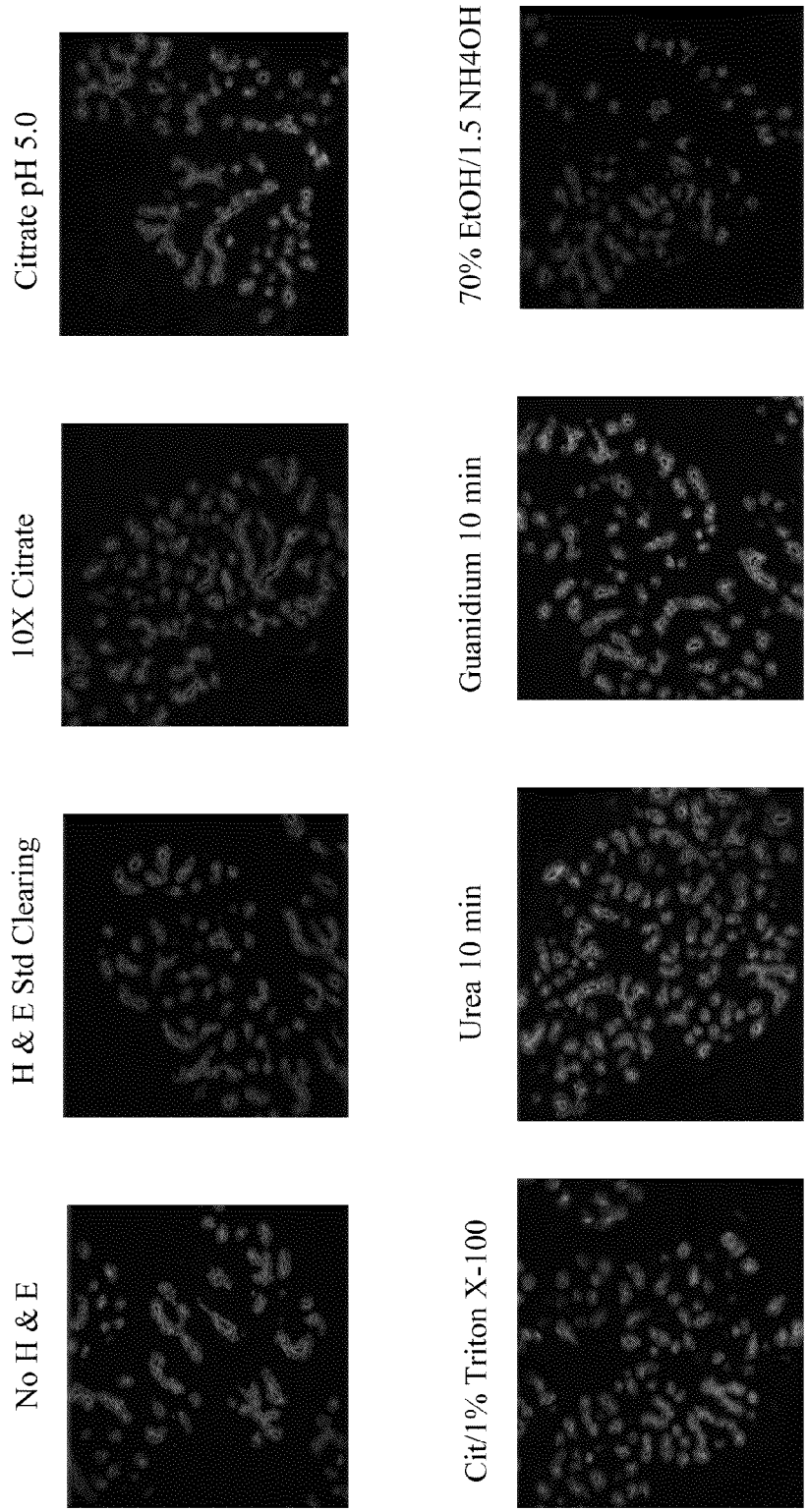
FIG. 10 shows grayscale images of pan-cytokeratin staining with Cy3-labeled AE1 antibody on the slides bleached by PICB (shown in FIG. 9)

In some embodiments, eosin signal may be partially removed during the antigen retrieval process before application of PICB to remove the residual signal. The antigen process itself or other washings steps using a variety of additives are unable to remove all eosin. FIG. 8. shows various unsuccessful attempts at removing the residual eosin fluorescence by making changes to the slide processing process (slide clearing and antigen retrieval) for immunohistochemistry by changing salt concentration, pH, addition of other salts or protein denaturants indicating PICB is necessary to remove the signal as shown in FIG. 9 while maintaining tissue antigenicity as shown by staining the same slides with a Cy3-labeled panCK (Cy3-AE1) antibody (FIG. 10).

In some embodiments, aside from the sample preparation procedures discussed above, the biological sample may be subjected to further treatment following H&E removal. For example, in some embodiments, the tissue section may be subjected to a blocking step to minimize any non-specific binding. Following the preparation of the sample, the sample may be contacted with a binder solution (e.g., labeled-antibody solution in an immunofluorescence procedure) for a sufficient period of time and under conditions suitable for binding of binder to the target protein (e.g., antigen in an immunofluroescence procedure).

In some embodiments, the biological sample may be contacted with more than one binder in the contacting step. The plurality of binders may be capable of binding different target proteins in the biological sample. For example, a biological sample may include two target proteins: target1 and target2 and two sets of binders may be used in this instance: binders1 (capable of binding to target1) and binders2 (capable of binding to target2). As such, plurality of binders may be contacted with the biological sample simultaneously. For example staining with different fluorescently-labeled antibodies such as AR, ER, p53, Her2, smooth muscle actin, keratin, and pan-cadherin biomarkers, as a single mixture). The method further includes detecting signals from the binder, the one or more additional binders generating an image of the sample. A photo-induced chemical bleaching agent is applied thereby initiating a photoreaction that modifies both the H&E signal as well as that of one or more binders.

Figure 11:
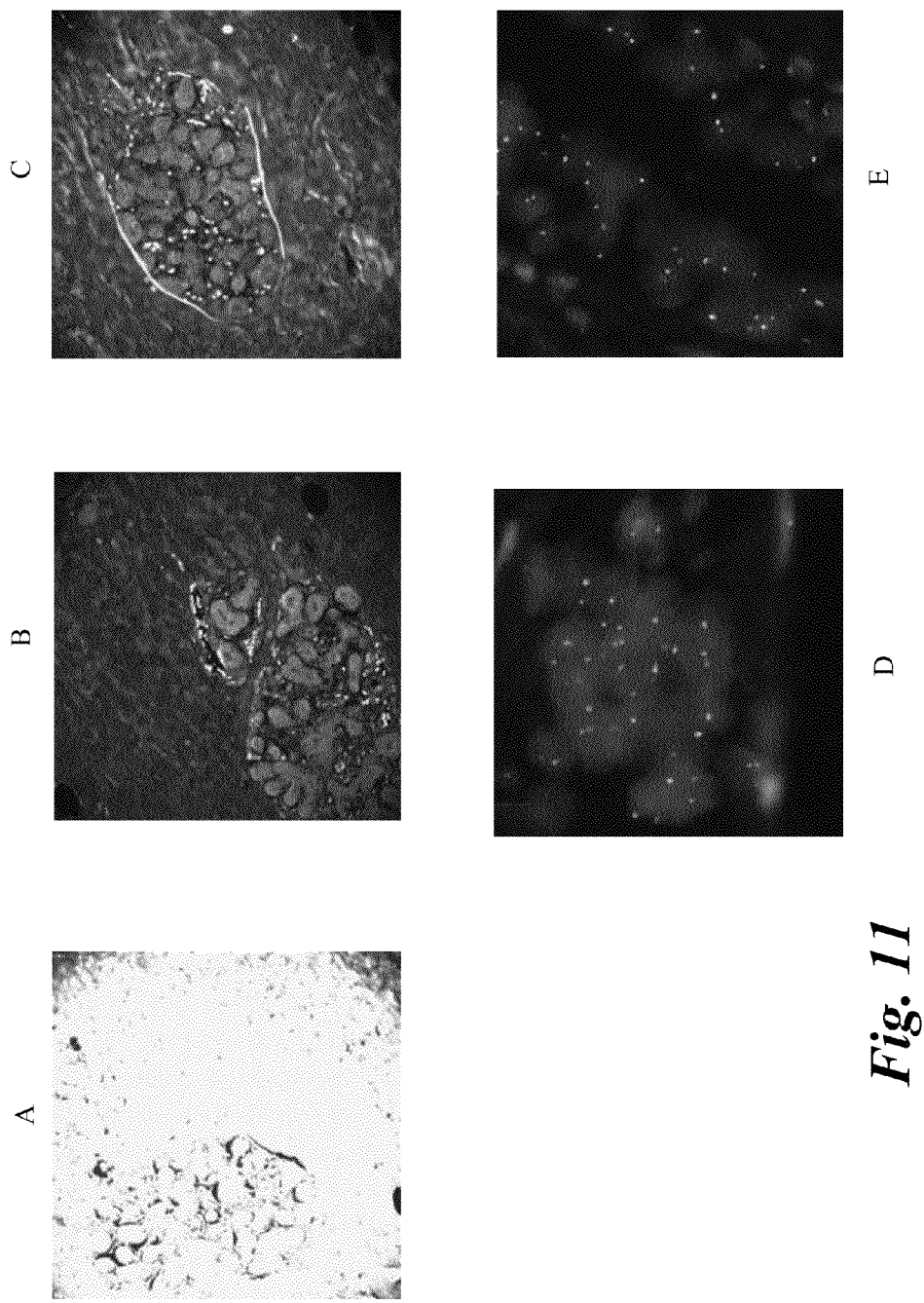
FIG. 11 shows FISH on PICB bleached H&E slide is comparable to FISH on a control slide that was not subjected to H&E staining.

In some embodiments, the sample may then undergo further sequential staining and detection of targets in multiple rounds of staining and signal removal. As such the method is applicable to using IHC, IF or FISH after a slide has been subjected to H&E staining. For example, FIG. 11 shows a fluorescence based image of an H&E stained slide (a) which after H&E removal using both washing and PICB steps was subjected to FISH with HER2 (R) and CEP17 (G) probes. A non-H&E stained slide was used as control. As the figure shows, after bleaching the residual fluorescence of the bleached slide which was treated with 40 mM dicyclopentyldiphenylborate lithium salt for 15 min 24 W lamp (b) is comparable to the tissue autofluorescence of the control slide (c) showing autofluorecence. Both slides (b and c) provide good staining with FISH probes (d and e respectively).

As such, the method includes but is not limited to methods that may also include detection and analysis of biological samples containing multiple targets and binding at least one probe having a binder coupled for example, to an enzyme to one or more target present in the sample. In yet other embodiments, the methods described above provide a series of at least two images depicting optically labeled biological targets which may be observed, in an observing step using a variety of methods.

In some embodiments, a control probe may be employed in the methods disclosed herein to provide for co-registration of multiple molecular information (obtained through the iterative probing steps) and the morphological information (obtained, e.g., using DAPI). In some embodiments, methods disclosed herein may include co-registration of multiple fluorescent images with bright-field morphological images obtained using the aforementioned H&E protocol. In some embodiments, the probes employed in the iterative probing steps may not have any common compartmental information that may be used to register with the initial H&E images. A control probe like a DAPI nuclear stain may be employed to co-register the nucleus stained with hematoxylin in the bright-field images with the fluorescent images. The fluorescent images and the bright-field images may be co-registered using image registration algorithms that may be grouped in two categories: intensity-based and feature-based techniques.

In some embodiments, the imaging, which may also be referred to as observing steps, include co-localizing at least two targets in the sample. Methods for co-localizing targets in a sample are described in U.S. patent application Ser. No. 11/686,649, entitled "System and Methods for Analyzing Images of Tissue Samples", filed on Mar. 15, 2007; U.S. patent application Ser. No. 11/500,028, entitled "System and Method for Co-Registering Multi-Channel Images of a Tissue Micro Array", filed on Aug. 7, 2006; U.S. patent application Ser. No. 11/606,582, entitled "System and Methods for Scoring Images of a Tissue Micro Array, filed on Nov. 30, 2006, and U.S. application Ser. No. 11/680,063, entitled Automated Segmentation of Image Structures, filed on Feb. 28, 2007, now U.S. Pat. No. 8,036,462, issued on Oct. 11, 2011, each of which is herein incorporated by reference.

In the observing steps, a signal from a signal generator may be detected using a detection system. The nature of the detection system used may depend upon the nature of the signal generators used. The detection system may include an, a charge coupled device (CCD) detection system a fluorescent detection system, an electrical detection system, a photographic film detection system, a chemiluminescent detection system, an enzyme detection system, an optical detection system, a near field detection system, or a total internal reflection (TIR) detection system.

One or more of the aforementioned techniques may be used to observe one or more characteristics of a signal from a signal generator (coupled with a binder or coupled with an enzyme substrate). In some embodiments, signal intensity, signal wavelength, signal location, signal frequency, or signal shift may be determined using one or more of the aforementioned techniques. In some embodiments, one or more aforementioned characteristics of the signal may be observed, measured, and recorded.

In some embodiments, one or more of the aforementioned may be automated and may be performed using automated systems. In some embodiments, all the steps may be performed using automated systems.

The methods disclosed herein may find applications in analytic, diagnostic, and therapeutic applications in biology and in medicine. In some embodiments, the methods disclosed herein may find applications in histochemistry, particularly, immunohistochemistry. Analysis of cell or tissue samples from a patient, according to the methods described herein, may be employed diagnostically (e.g., to identify patients who have a particular disease, have been exposed to a particular toxin or are responding well to a particular therapeutic or organ transplant) and prognostically (e.g., to identify patients who are likely to develop a particular disease, respond well to a particular therapeutic or be accepting of a particular organ transplant). The methods disclosed herein, may facilitate accurate and reliable analysis of a plurality (e.g., potentially infinite number) of targets (e.g., disease markers) from the same biological sample.

EXAMPLES

The following examples are intended only to illustrate methods and embodiments in accordance with the invention, and as such should not be construed as imposing limitations upon the claims.

Example 1

Preparation of Tissue Samples

Human breast tissue array samples were obtained as tissue slides embedded in paraffin from Clarient, Huntsville, Ala. Slides were baked at 60° C. for 15 minutes and then H&E stained.

Example 2

H&E Staining

All the slides were stained with hematoxylin and eosin following the standard regressive protocol listed below. After staining, images were obtained as described below in Table 1. In the procedure the slide with tissue is baked at 60° C. for 15 minutes prior to the first XYLENE step. The Hematoxylin and Eosin were filtered before each use. Coverslip was applied directly out of xylene to prevent the slide from drying before coverslipping.

TABLE 1

Standard Regressive protocol H&E Staining

| Solution | Time | Vendor | Manufacture/Catalog # |
|---|---|---|---|
| Xylene | 5 minutes | Fisher Sci. | Fisher Chemical #C8H10 |
| Xylene | 3 minutes | Fisher Sci. | Fisher Chemical #C8H10 |
| 100% Alcohol | 1 minute | VWR | EMD-HARLECO, 100% Alcohol blend #34172-020 |
| 100% Alcohol | 1 minute | VWR | EMD-HARLECO, 100% Alcohol blend #34172-021 |
| 95% Alcohol | 1 minute | VWR | EMD-HARLECO, Dehydration Alcohol 95%, #65348 |
| 95% Alcohol | 1 minute | VWR | EMD-HARLECO, Dehydration Alcohol 95%, #65349 |
| 80% Alcohol | 1 minute | VWR | EMD-HARLECO, Dehydration Alcohol 95%, #65350 |
| DI Water | 20-30 seconds | | |
| HEMATOXYLIN | 5 minutes | VWR | EMD-HARLECO, Gill Modified, solution 2, #65066-85 |
| DI Water | 5 quick dips | | |
| DI Water | 5 quick dips | | |
| 1% Acid alcohol | 1 quick dip | VWR | 99% 70% alcohol, 1% Hydrochloric Acid-EMD CHEMICALS #HX0603P-5 |
| DI Water | 5 quick dips | | |
| DI Water | 5 quick dips | | |
| Blueing | 2 minutes | VWR | EMD-HARLECO Staining Blueing Reagent #65354-85 |
| Running Water | 2 minutes | | |
| DI Water | 5 quick dips | | |
| 95% Alcohol | 30 seconds | VWR | EMD-HARLECO, Dehydration Alcohol 95%, #65348 |
| Eosin Y | 1½ minutes | VWR | EMD-HARLECO, 1% alcoholic solution #588X-75 |
| 95% Alcohol | 10 dips | VWR | EMD-HARLECO, Dehydration Alcohol 95%, #65348 |
| 95% Alcohol | 10 dips | VWR | EMD-HARLECO, Dehydration Alcohol 95%, #65348 |
| 100% Alcohol | 30 seconds | VWR | EMD-HARLECO, 100% Alcohol blend #34172-020 |
| 100% Alcohol | 30 seconds | VWR | EMD-HARLECO, 100% Alcohol blend #34172-020 |
| Xylene | 3 minutes | Fisher Sci. | Fisher Chemical #C8H10 |

Example 3

Imaging

Brightfield and Fluorescence images were taken for all the slides using Leica brightfield microscope and Olympus microscope respectively. For fluorescence, eosin stained images were collected in Cy2 (Ex: 482/35, Em: 536/40), Cy3 (Ex: 531/40, Em: 593/40), and Cy5 (Ex: 628/40, Em: 692/40) channels.

Example 4

Tissue Rehydration and Permeabilization

After imaging, samples were hydrated by washing in four solutions of ethanol with concentrations decreasing in the order of 100%, 95%, 70%, and 50% followed by a wash with 1× phosphate buffer saline (PBS, pH 7.4). After rehydration, the slides were washed with 1×PBS. A ten minute wash in 0.3% Triton X-100 in PBS was performed for membrane permeabilization of the tissue, followed by a wash with 1×PBS. The slides were then subjected to different buffers to attempt H&E removal.

Example 5

Antigen Retrieval

Hydrated slides were treated with dual-buffer heat-induced epitope retrieval. Slides were immersed in a pre-heated 70° C. Citrate Buffer pH 6.0 (Vector Unmasking Solution), further heated in a pressure cooker to a temperature of 110° C., held at this temperature for 4 minutes, and then gradually cooled (final temperature of 96° C.). Slides were in Citrate Buffer for a total of twenty minutes and then transferred to hot (96° C.) Tris-EDTA Buffer pH 9.0 and allowed to stand in the cooker at atmospheric pressure with gradual cooling for twenty minutes. This was followed by cooling down at room temperature for ten minutes and a series of washes in 1×PBS. Slides were imaged by brightfield and fluorescence microscopy. While brightfield images showed practically complete removal of hematoxylin and eosin colors, bright fluorescence was observed from residual eosin.

Example 6

Attempted Removal of H&E Without PICB

Slides were additionally subjected to following conditions in an attempt to remove H&E. 10× citrate (instead of standard 1× citrate during antigen retrieval for standard time of 20 minutes), citrate pH 5.0 (instead of standard citrate pH 6.0 during antigen retrieval for standard time of 20 minutes), citrate made in 1% triton X-100 (instead of standard citrate made in PBS during antigen retrieval for standard time of 20 minutes), 100 mM urea pH 4.5 (10 minute wash followed by 3 brief water washes before proceeding to antigen retrieval), 100 mM guanidinium pH 5.0 (10 minute wash followed by 3 brief water washes before proceeding to antigen retrieval), 70% ethanol in 1.5M NH4OH (instead of 70% ethanol in water during rehydration for standard 2×5 minutes).

Example 7

Blocking

The Following antigen retrieval the slides were blocked against nonspecific binding by incubating overnight in a 10% donkey serum, 3% bovine serum albumin (BSA) solution at 4° C.

Example 8

Residual Eosin Bleaching

All H & E slides after blocking were treated with 40 mM of Dicyclopentyl diphenylborate (500 μl) and irradiated with 500 nm light for 30 minutes. Washed with 3×PBS to remove the residual borate Example 9. Protein Staining and Imaging

Example 9

Immuno Staining

Slides were stained with DAPI and cover slipped. Images were taken at 20× prior to protein staining to see the autofluorescence of eosin in Cy2, Cy3 and Cy5 channels. Slides were decoverslipped in 1×PBS and stained with cytokeratin AE1-Cy3 conjugate diluted in 3% BSA in 1×PBS Incubation was for one hour at room temperature. After incubation, a series of washes in 1×PBS removed excess antibodies and slides were cover slipped. The samples were imaged.

Example 10

H&E and Fluoresence In Situ Hybridization (FISH) on the Same Slide

Steps 1-7 were performed as described above in the Examples 1-5, 7 & 8. FISH protocol was then applied. Slides were decoverslipped after imaging and immersed in a prewarmed 0.1% pepsin solution for 8 minutes then placed in room temperature PBS for 2 minutes. Samples were re-fixed in 4% formalin for 10 minutes then washed 2×5 minutes in PBS. Slides were dehydrated in ethanol series 50%, 70%, and 95%, 2 minutes each and allowed to dry on benchtop for 10 minutes. Pre-mixed dual Her2/CEP17 probe was vortexed, spun, and added to samples. Samples were coverslipped and sealed with a rubber sealant per usual practice. After allowing rubber cement to cure for 10 minutes, probes were hybridized in Thermobrite cycler: 80° C. denaturation for 10 minutes followed by 37° C. incubation overnight. Rubber cement removed and slides decoverslipped in preheated 37° C. 2×SSC for 5 minutes then transferred into preheated 72° C. 2×SSC, 0.3% NP-40 for 2 minutes. Slides were washed 2×2 minutes with 2×SSC, removed from buffer to dry, coverslipped with 4% DABCO in 90% glycerol/2×SSC, and imaged on an Olympus IX81 fluorescence microscope using a 40× objective for dapi (2 ms), spectrum green (CEP17-200 ms), and spectrum orange (Her2-400 ms). A z-stack value of 12, gain of 10, and step size of 0.75μ were used.

What is claimed is:

1. A sequential method of preparing a hematoxylin and eosin stained biological sample for analysis comprising:
   (a) providing a hematoxylin and eosin stained biological sample containing multiple targets;
   (b) observing the hematoxylin and eosin si al from the stained biological sample;
   (c) removing the hematoxylin and partially removing the eosin by washing the sample;
   (d) contacting the sample with an electron transfer reagent where the electron transfer reagent is a borate salt represented by the following structural formula:

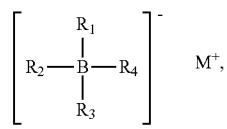

wherein:
   each R1, R2, and R3 is, independently, an alkyl, an alkenyl, an akynyl, an aryl or a heteroaryl, wherein said alkyl, alkenyl, alkynyl, aryl or heteroaryl is optionally substituted with one or more substituents selected from the group consisting of (C1-C4)alkyl, (C1-C4)alkoxy, (C1-C4)alkylamino, amino, hydroxyl, cyano, halogen, or nitro,
   R4 is an alkyl, an alkenyl, or an akynyl, wherein said alkyl, alkenyl, or alkynyl is optionally substituted with one or more substituents selected from the group consisting of (C1-C4)alkyl, aryl, (C1-C4)alkoxy, (C1-C4)alkylamino, amino, hydroxyl, cyano, halogen, or nitro, and
   M+ is selected from the group consisting of organic and inorganic cations;
   (e) irradiating the sample of step (d) to remove residual fluorescence.

2. The method of claim 1, wherein irradiating the sample in step (e) is accomplished by exposing the sample to light of 350 nm-1.3 μM in wavelength.

3. The method of claim 2, wherein irradiating the sample in step (e) is accomplished by exposing the sample to light of 400-700 nm in wavelength.

4. The method of claim 1, wherein irradiating the sample in (e) is carried out in the presence of a buffer at pH of 5-9.

5. The method of claim 1 wherein step (e) is carried out at the temperature of 4-50° C.

6. The method of claim 1, wherein step (e) is performed for about 20 seconds to about 15 minutes.

7. The method of claim 1 wherein each $R_1$, $R_2$, and $R_3$ is each independently an optionally substituted aryl and $R_4$ is an optionally substituted alkyl.

8. The method of claim 7 wherein each $R_1$, $R_2$, and $R_3$ is phenyl and $R_4$ is butyl, or benzyl.

9. The method of claim 1 wherein M+ is an inorganic cation selected from the group consisting of $Li^+$, $Na^+$ or $K^+$.

10. The method of claim 1 further comprising the steps of:
    (f) binding at least one probe capable of signal generation to one or more targets to the sample of step (e);
    (g) observing a signal from the probe bound in step (f); and
    (h) optionally contacting the sample with a bleaching agent and repeating steps (f) through (g).

11. The method of claim 10 wherein the bleaching agent is a photoactivated chemical bleaching agent and the step (h) further comprises irradiating the sample by exposing the sample to light of 350 nm-1.3 μM in wavelength.

12. The method of claim 11, wherein irradiating the sample is accomplished by exposing the sample to light of 400-700 nm in wavelength.

13. The method of claim 10, wherein the probe in step (f) comprises a fluorescent signal generator, and the signal observed in step (g) is a fluorescent signal.

14. The method of claim 10, wherein steps (f)-(h) are repeated two or more times.

15. The method of claim 10, further comprising measuring one or more intensity values of the signal observed in observing step (g).

16. The method of claim 15 further comprising correlating the intensity value with an amount of target present in the sample.

17. The method of claim 10, wherein the electron transfer agent in step (d) is the same as the bleaching agent in step (h) and step (h) further comprises irradiating the sample by exposing the sample to light of 350 nm-1.3 µM in wavelength.

18. A sequential method of probing multiple targets in a hematoxylin and eosin stained biological sample comprising:
(a) providing a hematoxylin and eosin stained biological sample containing multiple targets;
(b) observing the hematoxylin and eosin signal from the stained biological sample;
(c) optionally removing the hematoxylin and partially removing the eosin by washing the sample;
(d) subjecting the sample to an antigen retrieval process to expose one or more antigens in the region of interest;
(e) optionally applying a blocking reagent to block against nonspecific binding of one or more antigens;
(f) contacting the sample with an electron transfer agent reagent where the electron transfer reagent is a borate salt represented by the following structural formula:

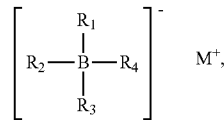

wherein:
each R1, R2, and R3 is, independently, an alkyl, an alkenyl, an akynyl, an aryl or a heteroaryl, wherein said alkyl, alkenyl, alkynyl, aryl or heteroaryl is optionally substituted with one or more substituents selected from the group consisting of (C1-C4)alkyl, (C1-C4)alkoxy, (C1-C4)alkylamino, amino, hydroxyl, cyano, halogen, or nitro,
R4 is an alkyl, an alkenyl, or an akynyl, wherein said alkyl, alkenyl, or alkynyl is optionally substituted with one or more substituents selected from the group consisting of (C1-C4)alkyl, aryl, (C1-C4)alkoxy, (C1-C4)alkylamino, amino, hydroxyl, cyano, halogen, or nitro, and
M+ is selected from the group consisting of organic and inorganic cations;
(g) irradiating the sample of step (f);
(h) binding at least one probe capable of signal generation to one or more targets present in the sample of step (g);
(i) observing a signal from the probe bound in step (h); and
(j) optionally contacting the sample with a bleaching agent and repeating steps (h) through (i).

19. The method of claim 18 wherein step (h) wherein the probe is a protein stain.

20. The method of claim 18 wherein the bleaching agent is a photoactivated chemical bleaching agent and the step (j) further comprises irradiating the sample by exposing the sample to light of 350 nm-1.3 µM in wavelength.

21. The method of claim 18, wherein each $R_1$, $R_2$, and $R_3$ is an independently optionally substituted aryl and $R_4$ is an optionally substituted alkyl.

22. The method of claim 21, wherein each $R_1$, $R_2$, and $R_3$ is phenyl and $R_4$ is butyl or benzyl.

23. The method of claim 18 wherein M+ is an inorganic cation selected from the group consisting of Li+, Na+ or K+.

24. The method of claim 18 wherein the electron transfer agent in step (f) is the same as the bleaching agent in step (j) and step (j) further comprises irradiating the sample by exposing the sample to light of 350 nm-1.3 µM in wavelength.

25. A sequential method of probing multiple targets in a hematoxylin and eosin stained biological sample comprising:
(a) providing a hematoxylin and eosin stained biological sample containing multiple targets;
(b) observing the hematoxylin and eosin signal from the stained biological sample;
(c) removing the hematoxylin and partially removing the eosin by washing the sample;
(d) contacting the sample with an electron transfer agent reagent where the electron transfer reagent is a borate salt represented by the following structural formula:

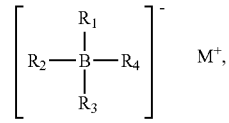

wherein:
each R1, R2, and R3 is, independently, an alkyl, an alkenyl, an akynyl, an aryl or a heteroaryl, wherein said alkyl, alkenyl, alkynyl, aryl or heteroaryl is optionally substituted with one or more substituents selected from the group consisting of (C1-C4)alkyl, (C1-C4)alkoxy, (C1-C4)alkylamino, amino, hydroxyl, cyano, halogen, or nitro,
R4 is an alkyl, an alkenyl, or an akynyl, wherein said alkyl, alkenyl, or alkynyl is optionally substituted with one or more substituents selected from the group consisting of (C1-C4)alkyl, aryl, (C1-C4)alkoxy, (C1-C4)alkylamino, amino, hydroxyl, cyano, halogen, or nitro, and
M+ is selected from the group consisting of organic and inorganic cations;
(e) irradiating the sample of step (d) to remove the residual eosin fluorescence
(f) binding at least one probe capable of signal generation to one or more targets present in the sample of step (e);
(g) observing a signal from the probe bound in step (f); and
(h) optionally subjecting the sample to a bleaching agent, DNA denaturant, heat, or a combination thereof and repeating steps (f) through (h).

26. The method of claim 25, wherein each $R_1$, $R_2$, and $R_3$ is each independently an optionally substituted aryl and $R_4$ is an optionally substituted alkyl.

27. The method of claim 26, wherein each $R_1$, $R_2$, and $R_3$ is phenyl and $R_4$ is butyl or benzyl.

28. The method of claim 25 wherein M+ is an inorganic cation selected from the group consisting of Li+, Na+ or K+.

29. The method of claim 25 wherein the electron transfer agent in step (d) is the same as the bleaching agent in step (h) and step (h) further comprises irradiating the sample by exposing the sample to light of 350 nm-1.3 µM in wavelength.

30. A method according to claim 27 wherein the at least one probe is a FISH probe.

* * * * *